US007244617B2

(12) United States Patent
Fang et al.

(10) Patent No.: US 7,244,617 B2
(45) Date of Patent: *Jul. 17, 2007

(54) DIMINISHING VIRAL GENE EXPRESSION BY PROMOTER REPLACEMENT

(75) Inventors: Bingliang Fang, Houston, TX (US); Jack A. Roth, Houston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 236 days.

This patent is subject to a terminal disclaimer.

(21) Appl. No.: 10/677,727

(22) Filed: Oct. 2, 2003

(65) Prior Publication Data

US 2005/0026139 A1 Feb. 3, 2005

Related U.S. Application Data

(63) Continuation of application No. 09/650,946, filed on Aug. 29, 2000, now Pat. No. 6,630,344, which is a continuation of application No. 08/968,014, filed on Nov. 12, 1997, now Pat. No. 6,110,744.

(60) Provisional application No. 60/030,675, filed on Nov. 13, 1996.

(51) Int. Cl.
*C12N 15/861* (2006.01)
*C12N 15/12* (2006.01)
*C12N 15/34* (2006.01)

(52) U.S. Cl. ............... 435/456; 435/320.1; 536/23.72; 536/23.5

(58) Field of Classification Search ..................... None
See application file for complete search history.

(56) References Cited

U.S. PATENT DOCUMENTS

| 5,527,676 | A | 6/1996 | Vogelstein et al. ............. 435/6 |
| 5,998,205 | A | 12/1999 | Hallenbeck et al. ......... 435/325 |
| 6,306,652 | B1 | 10/2001 | Fallaux et al. .............. 435/325 |
| 6,630,344 | B1 * | 10/2003 | Fang et al. .............. 435/320.1 |
| 6,899,870 | B1 * | 5/2005 | McDonnell et al. ....... 424/93.2 |

FOREIGN PATENT DOCUMENTS

| FR | 2729674 | 7/1996 |
| WO | WO 96/17053 | 6/1996 |

OTHER PUBLICATIONS

Imler Adenovirus vectors as recombinant viral vaccines. Vaccine vol. 13 pp. 1143-1151 (1995).*
Gilardi et al. The E4 promoter of adenovirus type 2 contains an E1A dependent cis-acting element. Nucleic Acids Res. vol. 14 pp. 9035-9049.*
Abel et al., "DNA elements responsive to auxin," (Review), *Bioessays*, 18(8):647-54, Aug. 1996.

Abel et al., "The PS-IAA4/5-like family of early auxin-inducible mRNAs in *Arabidopsis thaliana*," *J. Mol. Biol.*, 251(4):533-49, Aug. 1995.
Adler et al., "UV irradiation and heat shock mediate JNK activation via alternate pathways," *J. Biol.. Chem.*, 270(44):26071-26077, 1995.
Ali-Osman et al., "Enhanced repair of a cisplatin-damaged reporter chloramphenicol-O-acetyltransferase gene and altered activities of DNA polymerases α and β, and DNA ligase in cells of human malignant glioma following in vivo cisplatin therapy," *J. Cell. Biochem.*, 54:11-19, 1994.
Baker et al., "Suppression of human colorectal carcinoma cell growth by wild-type p53," *Science*, 249:912-915, Aug. 1990.
Baverstock and Will, "Evidence of the dominance of direct excitation of DNA in the formation of strand breaks in cells following irradiation," *Int. J. Radiat. Biol.*, 55(4):563-568, 1989.
Berkner, "Development of adenovirus vectors for the expression of heterologous genes," *Biotechniques*, 6:616-629, 1988.
Berkner et al., "Generation of adenovirus by transfection of plasmids," *Nucleic Acids Research*, 11:6003-6020, 1983.
Bett et al., "An efficient and flexible system for construction of adenovirus vectors with insertions or deletions in early regions 1 and 3," *Medical Sciences*, 91:8802-8806, 1994.
Bigner et al., "Cyogenetics of human brain tumors," *Cancer Genet Cytogenet*, 47:141-154, 1990.
Bigner et al., "Heterogeneity of genotypic and phenotypic characteristics of fifteen permanent cell lines derived from human gliomas," *J. Neuropathol. & Experimental Neurol.*, XL(3):201-229, May/Jun. 1981.
Brand and Perrimon, "Targeted gene expression as a means of altering cell fates and generating dominant phenotypes," *Development*, 118:401-415, 1993.
Braselmann et al., "A selective transcription induction system for mammalian cells based on Gal4-estrogen receptor fusion proteins," *Proc. Natl. Acad. Sci. USA*, 90:1657-1661, Mar. 1993.
Clarke et al., "Thymocyte apoptosis induced by p53-dependent and independent pathways," *Nature*, 362:849-852, Apr. 1993.
Di Leonardo et al., "DNA damage triggers a prolonged p53-dependent $G_1$ arrest and long-term induction of Cip1 in normal human fibroblasts," *Genes & Dev.*, 8:2540-2551, 1994.
Donehower et al., "Deficiency of *p53* accelerates mammary tumorigenesis in *Wnt-1* transgenic mice and promotes chromosomal instability," *Genes and Development*, 9:882-895, 1995.

(Continued)

*Primary Examiner*—John S. Brusca
(74) *Attorney, Agent, or Firm*—Fulbright & Jaworski L.L.P.

(57) ABSTRACT

The present invention provides viral vectors that have been engineered to contain a synthetic promoter that controls at least one essential gene. The synthetic promoter is induced by a specific gene product not normally produced in the cells in which the viral vector is to be transferred. The vectors are propagated in producer or helper cells that express the inducing factor, thereby permitting the virus to replicate to high titer. The lack of the inducing factor in the target cells precludes viral replication, however, meaning that no vector toxicity or immunogenicity arises. Where the virus carries a gene of interest, this should provide for higher level expression for longer periods of time than with current vectors. Methods for making the vectors, helper cells, and their use in protein production, vaccines and gene therapy are disclosed.

28 Claims, 17 Drawing Sheets

OTHER PUBLICATIONS

El-Deiry et al., "*WAF1*, a potential mediator of p53 tumor suppression," *Cell*, 75:817-825, Nov. 1993.

El-Deiry et al., "*WAF1/CIP1* is induced in *p53*-mediated $G_1$ arrest and apoptosis," *Cancer Research*, 54:1169-1174, Mar. 1994.

Eliyahu et al., "p53—a potential suppressor gene?" *J. Cell. Biochem.*, UCLA Symposia on Molecular and Cellular Biology, Abstract I030, Feb.-Mar. 1990.

Evans et al., "Differential sensitivity to the induction of apoptosis by cisplatin in proliferating and quiescent immature rat thymocytes is independent of the levels of drug accumulation and DNA adduct formation," *Cancer Research*, 54:1596-1603, Mar. 1994.

Fang, Koch and Roth, "Diminishing adenovirus gene expression and viral replication by promoter replacement," *J Virol.*, 71(6):4798-4803, 1997.

Fang, Koch and Roth, "Replacing adenoviral E4 promoter with GAL4/TATA dramatically reduces viral gene expression," *Cancer Gene Therapy*, 3(6):S25, Abstract p. 54, 1996.

Fanjul et al., "A new class of retinoids with selective inhibition of AP-1 inhibits proliferation," *Nature*, 372:107-111, Nov. 1994.

Fischer et al., "GAL4 activates transcription in *Drosophila*," *Nature*, 332:853-856, Apr. 1988.

Fraval et al., "Increased sensitivity of UV-repair-deficient human cells to DNA bound platinum products which unlike thymine dimers are not recognized by an endonuclease extracted from *Micrococcus luteus*," *Mutation Research*, 51:121-132, 1978.

Fujiwara et al., "Induction of chemosensitivity in human lung cancer cells in vivo by adenovirus-mediated transfer of the wild-type *p53* gene," *Cancer Research*, 54:2287-2291, May 1994.

Gipp et al., "DNA damage induced in HT-29 colon cancer cells by exposure to 1-methyl-2-nitrosoimidazole, a reductive metabolite of 1-methyl-2-nitroimidazole," *Biochem. Pharmacol.*, Suppl., 42:S127-S133, 1991.

Gjerset et al., "Use of wild-type *p53* to achieve complete treatment sensitization of tumor cells expressing endogenous mutant p53," *Mol. Carcinogenesis*, 14:275-285, 1995.

Haj-Ahmad et al., "Development of a helper-independent human andenovirus vector and its use in the transfer of the herpes simplex thymiding kinase gene," *Journal of Virology*, 57:267-274, 1986.

Hayashi et al., "Expression of a thyroid hormone-responsive recombinant gene introduced into adult mice livers by replication defective adenovirus can be regulated by endogenous thyroid hormone receptor," *Journal of Biological Chemistry*, 269:23872-2375, 1994.

Hinds, "Biological consequences of mutation of the p53 proto-oncogene," a dissertation presented to the faculty of Princeton University in candidacy for the degree of Doctor of Philosophy, Oct. 1989.

International Search Report dated Apr. 20, 1998 (PCT/US97/20608)(INGN:033P).

Izumoto et al., "Homozygous deletions of p16$^{INK4A}$/MTS1 and p15$^{INK4B}$/MTS2 genes in glioma cells and primary glioma tissues," *Cancer Letters*, 97:241-247, 1995.

Jen et al., "Deletion of *p16* and *p15* genes in brain tumors," *Cancer Research*, 54:6353-6358, Dec. 1994.

Kaden et al., "High frequency of large spontaneous deletions of DNA in tumor-derived CHEF cells," *Proc. Natl. Acad. Sci. USA*, 86:2306-2310, Apr. 1989.

Kamb, "Cell-cycle regulators and cancer," *TIG*, 11(4):136-140, Apr. 1995.

Kashani-Sabet et al., "Cyclosporin A suppresses cisplatin-induced c-*fos* gene expression in ovarian carcinoma cells," *J. Biol. Chem.*, 265(19):11285-11288, Jul. 1990.

Kashani-Sabet et al., "Differential oncogene amplification in tumor cells from a patient treated with cisplatin and 5-fluorouracil," *Eur. J. Cancer*, 26(3):383-390, 1990.

Kimler, "The 9L rat brain tumor model for pre-clinical investigation of radiation-chemotherapy interactions," *J. Neuro-Oncology*, 20:103-109, 1994.

Krougliak and Graham, "Development of cell lines capable of complementing E1, E4, and protein IX defective adenovirus type 5 mutants," *Human Gene Therapy*, 6:1575-1586, Dec. 1995.

Lane, "p53, guardian of the genome," *Nature*, 358: 15-16, Jul. 1992.

Lee et al., "Molecular basis of tumor suppression by the human retinoblastoma gene," *J. Cell. Biochem.*, UCLA Symposia on Molecular & Cellular Biology, Abstract I001, Feb.-Mar. 1990.

Levine et al., "The p53 growth suppressor gene," *J. Cell. Biochem.*, UCLA Symposia on Molecular & Cellular Biology, Abstract, I029, Feb.-Mar. 1990.

Liu and Miller, "Eukaryotic DNA topoisomerases: two forms of type I DNA topoisomerases from HeLa cell nuclei," *Proc. Natl. Acad. Sci. USA*, 78(6):3487-3491, Jun. 1981.

Liu et al., "Cleavage of DNA by mammalian DNA topoisomerase II," *J. Biol. Chem.*, 258(24):15365-15370, Dec. 1983.

Lotem and Sachs, "Hematopoietic cells from mice deficient in wild-type p53 are more resistant to induction of apoptosis by some agents," *Blood*, 82(4):1092-1096, Aug. 1993.

Lowe et al., "*p53* status and the efficacy of cancer therapy in vivo," *Science*, 266:807-810, Nov. 1994.

Lowe et al., "p53-dependent apoptosis modulates the cytotoxicity of anticancer agents," *Cell*, 74:957-967, Sep. 1993.

Lukas et al., "Retinoblastoma-protein-dependent cell-cycle inhibition by the tumour suppressor p16," *Nature*, 375:503-506, Jun. 1995.

Mercer et al., "Antiproliferative effects of wild type human p53," *J. Cell. Biochem.*, UCLA Symposia on Molecular & Cellular Biology, Abstract I224, Feb.-Mar. 1990.

Mercer et al., "Negative growth regulation in a glioblastoma tumor cell line that conditionally expresses human wild-type p53," *Proc. Natl. Acad. Sci. USA*, 87:6166-6170, Aug. 1990.

Minna et al., "The molecular pathogenesis of lung cancer involves the accumulation of a large number of mutations in dominant oncogenes and multiple tumor suppressor genes (recessive oncogenes)," *J. Cell. Biochem.*, UCLA Symposia on Molecular & Cellular Biology, Abstract I003, Feb.-Mar. 1990.

Miyashita et al., "Tumor suppressor p53 is a regulator of *bcl-2* and *bax* gene expression in vitro and in vivo," *Oncogene*, 9:1799-1805, 1994.

Moulton et al., "MTS1/p16/CDKN2 lesions in primary glioblastoma multiforme," *American J. of Pathology*, 146(3):613-619, Mar. 1995.

Moynihan et al., "The role of chemotherapy in the treatment of primary tumors of the central nervous system," *Cancer Investigation*, 12(1):88-97, 1994.

Nigro et al., "Mutations in the *p53* gene occur in diverse human tumour types," *Nature*, 342:705-708, Dec. 1989.

Nishikawa et al., "Loss of p16$^{INK4}$ expression is frequent in high grade gliomas," *Cancer Research*, 55:1941-1945, May 1995.

Noble et al., "Effects of exogenous wild-type p53 on a human lung carcinoma cell line with endogenous wild-type p53," *Experimental Cell Research*, 203:297-304, 1992.

Ornitz et al., "Binary system for regulating transgene expression in mice: targeting *int-2* gene expression with yeast *GAL4/UAS* control elements," *Proc. Natl. Acad. Sci. USA*, 88:698-702, Feb. 1991.

Oshita and Saijo, "Rapid polymerase chain reaction assay to detect variation in the extent of gene-specific damage between cisplatin- or VP-16p-resistant and sensitive lung cancer cell lines," *Jpn. J. Cancer Res.*, 85:669-673, Jul. 1994.

Rogel et al., "p53 cellular tumor antigen: analysis of mRNA levels in normal adult tissues, embryos, and tumors," *Mol. and Cell. Biol.*, 5(10):2851-2855, Oct. 1985.

Sadowski et al., "*GAL4* fusion vectors for expression in yeast or mammalian cells," *Gene*, 11:137-141, 1992.

Sadowski et al., "GAL4-VP16 is an unusually potent transcriptional activator," *Nature*, 335:563-564, Oct. 1988.

Scanlon et al., "Cisplatin resistance in human cancers," *Pharmac. Ther.*, 52:385-406, 1991.

Scanlon et al., "Molecular basis of cisplatin resistance in human carcinomas: model systems and patients," *Anticancer Research*, 9:1301-1312, 1989.

Scanlon et al., "Overexpression of DNA replication and repair enzymes in cisplatin-resistant human colon carcinoma HCT8 cells and circumvention by azidothymidine," *Cancer Communications*, 1(4):269-275, 1989.

Shaw et al., "Induction of apoptosis by wild-type p53 in a human colon tumor-derived cell line," *Proc. Natl. Acad. Sci. USA*, 89:4495-4499, May 1992.

Tlsty, "Normal diploid human and rodent cells lack a detectable frequency of gene amplification," *Proc. Natl. Acad. Sci. USA*, 87:3132-3135, Apr. 1990.

Vaessen et al., "Different adenovirus E1A-controlled properties of transformed cells require different levels of E1A expression," *Gene*, 54:247-254, 1987.

Van Meir et al., "Release of an inhibitor of angiogenesis upon induction of wild type *p53* expression in glioblastoma cells," *Nature Genetics*, 8:171-176, Oct. 1994.

Vincent et al., "Gene therapy for malignant brain tumors," *Cancer Gene Therapy*, 1(4), Abstract V-80, Nov. 1994.

Vogelstein et al., "Genetic alterations accumulate during colorectal tumorigenesis," *J. Cell. Biochem.*, UCLA Symposia on Molecular & Cellular Biology, Abstract I004, Feb.-Mar. 1990.

Wahl et al., "Loss of normal p53 function confers sensitization to Taxol by increasing G2/M arrest and apoptosis," *Nature Medicine*, 2(1):72-79, Jan. 1996.

Wang et al., "A packaging cell line for propagation of recombinant adenovirus vectors containing two lethal gene-region deletions," *Gene Therapy*, 2:775-783, Aug. 1995.

Wang et al., "A regulatory system for use in gene transfer," *Proc. Natl. Acad. Sci. USA*, 91:8180-8184, Aug. 1994.

Wills et al., "Development and characterization of recombinant adenoviruses encoding human p53 for gene therapy of cancer," *Human Gene Therapy*, 5:1079-1088, 1994.

Wu and Levine, "p53 and E2F-1 cooperate to mediate apoptosis," *Proc. Natl. Acad. Sci. USA*, 91:3602-3606, Apr. 1994.

Yeh et al., "Efficient dual transcomplementation of adenovirus E1 and E4 regions from a 293-derived cell line expressing a minimal E4 functional unit," *J Virol.*, 70(1):559-565, 1996.

Yonish-Rouach et al., "Wild-type p53 induces apoptosis of myeloid leukaemic cells that is inhibited by interleukin-6," *Nature*, 352:345-347, Jul. 1991.

\* cited by examiner a
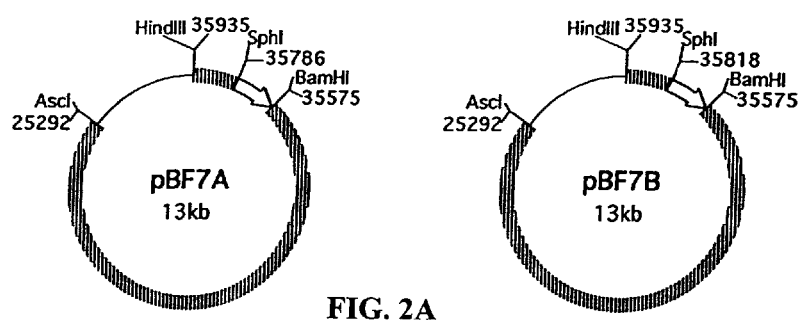
FIG. 2A
b
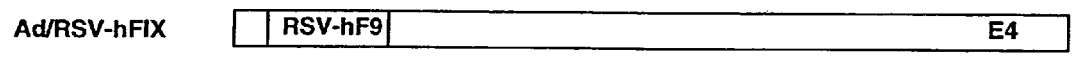
FIG. 2B

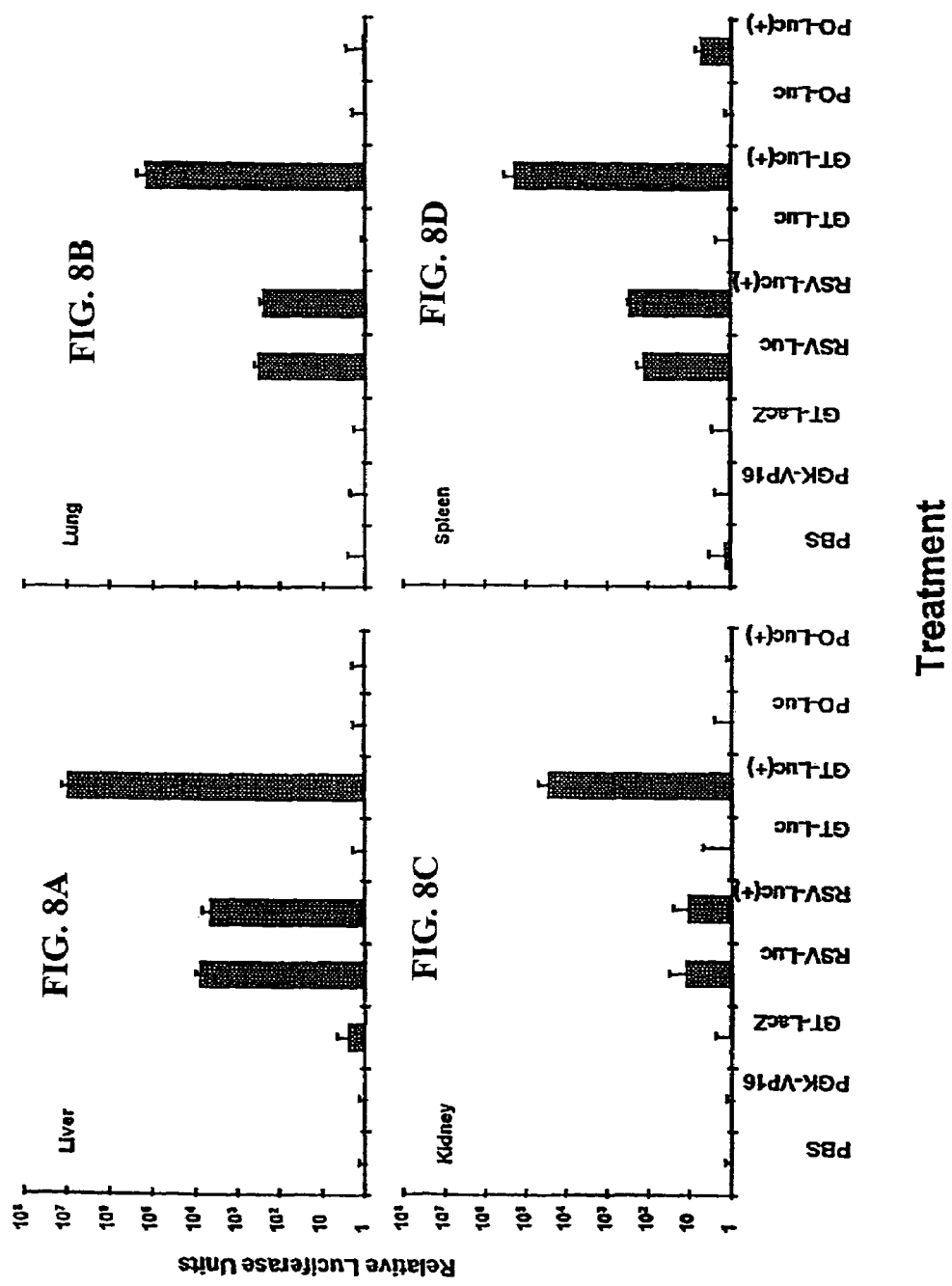

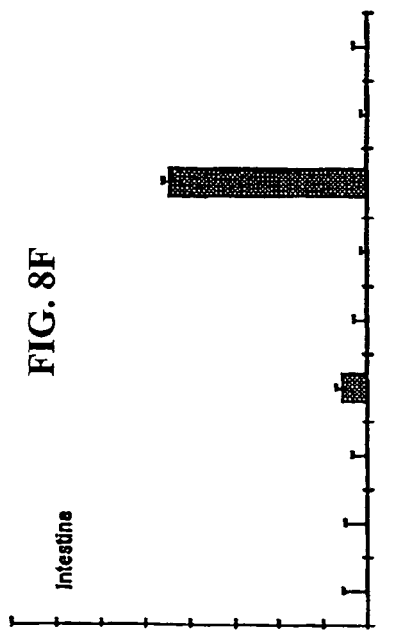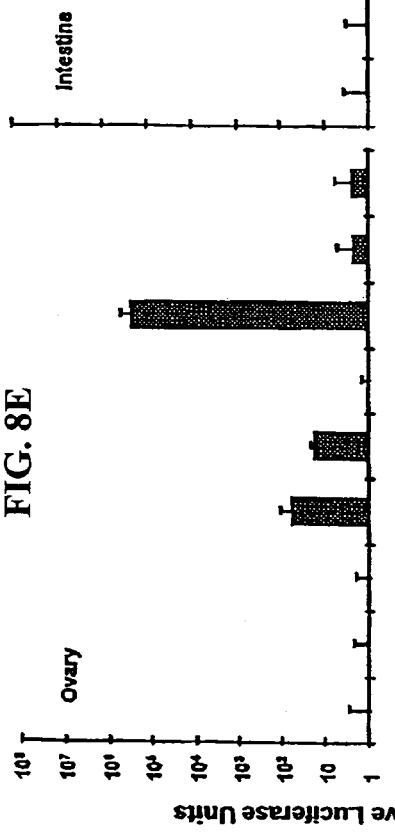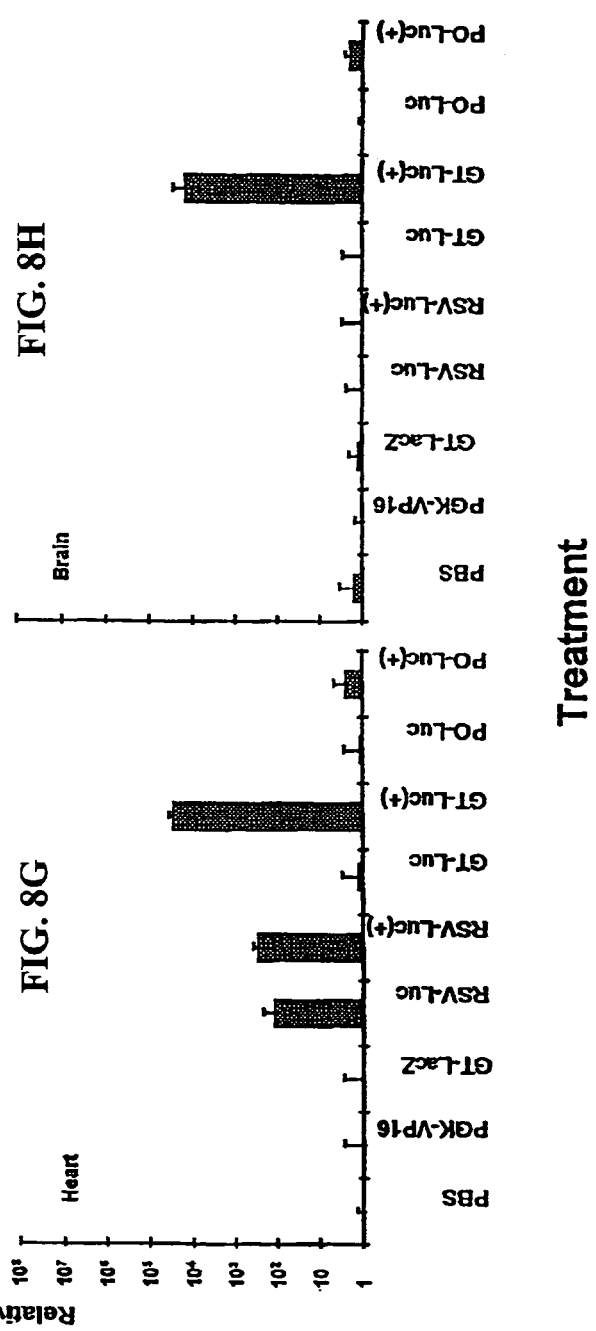
FIG. 8E FIG. 8F FIG. 8G FIG. 8H

FIG. 9A
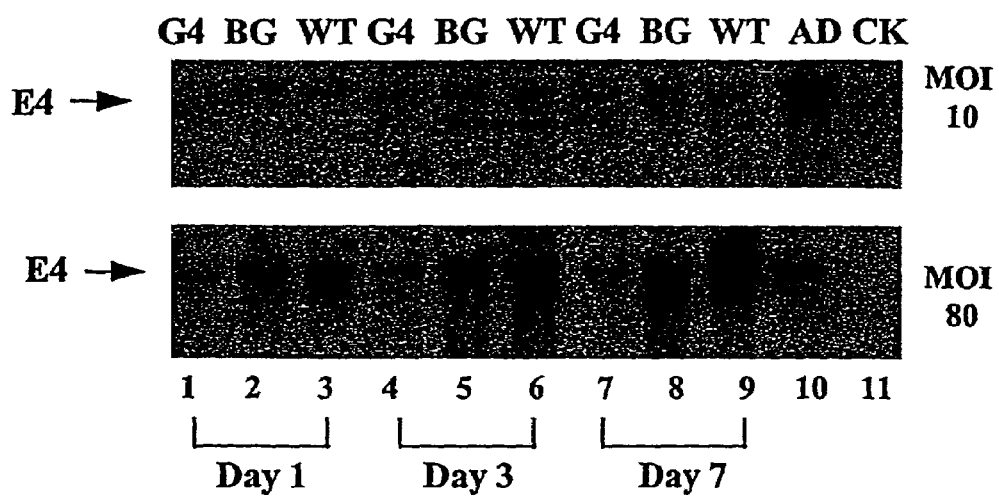
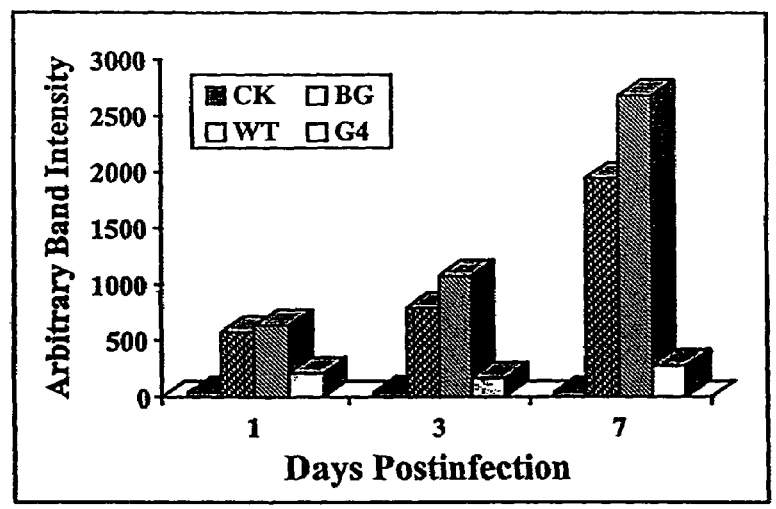
FIG. 9B

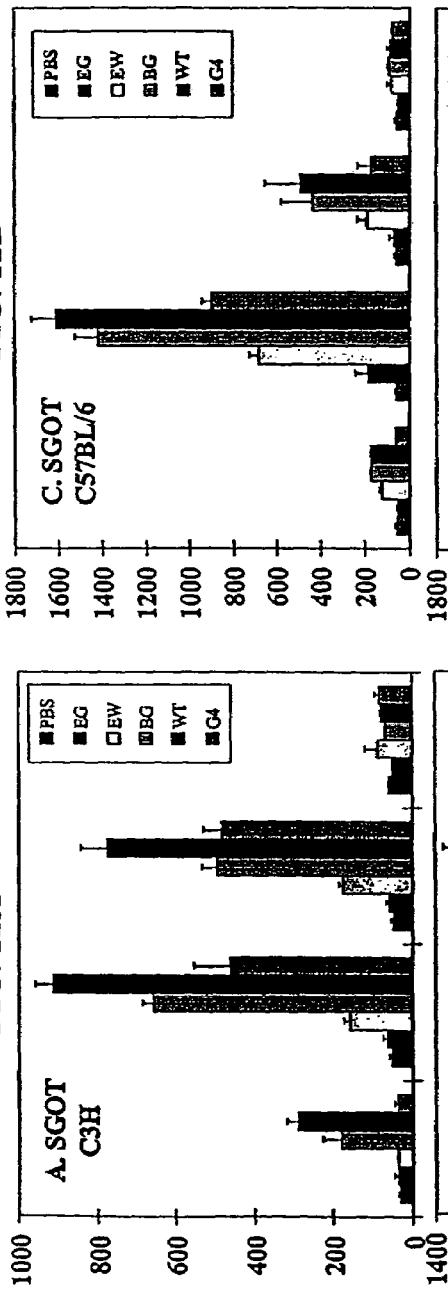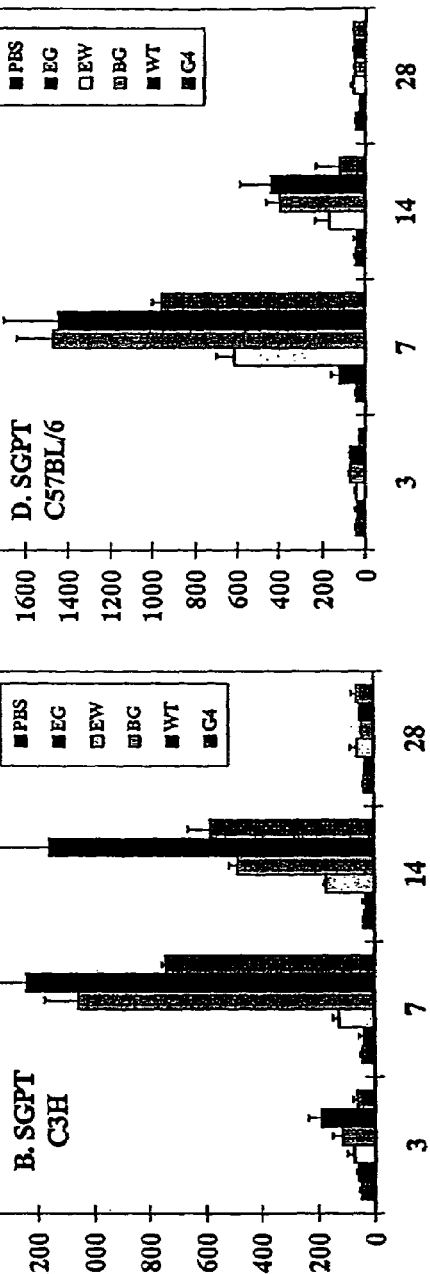

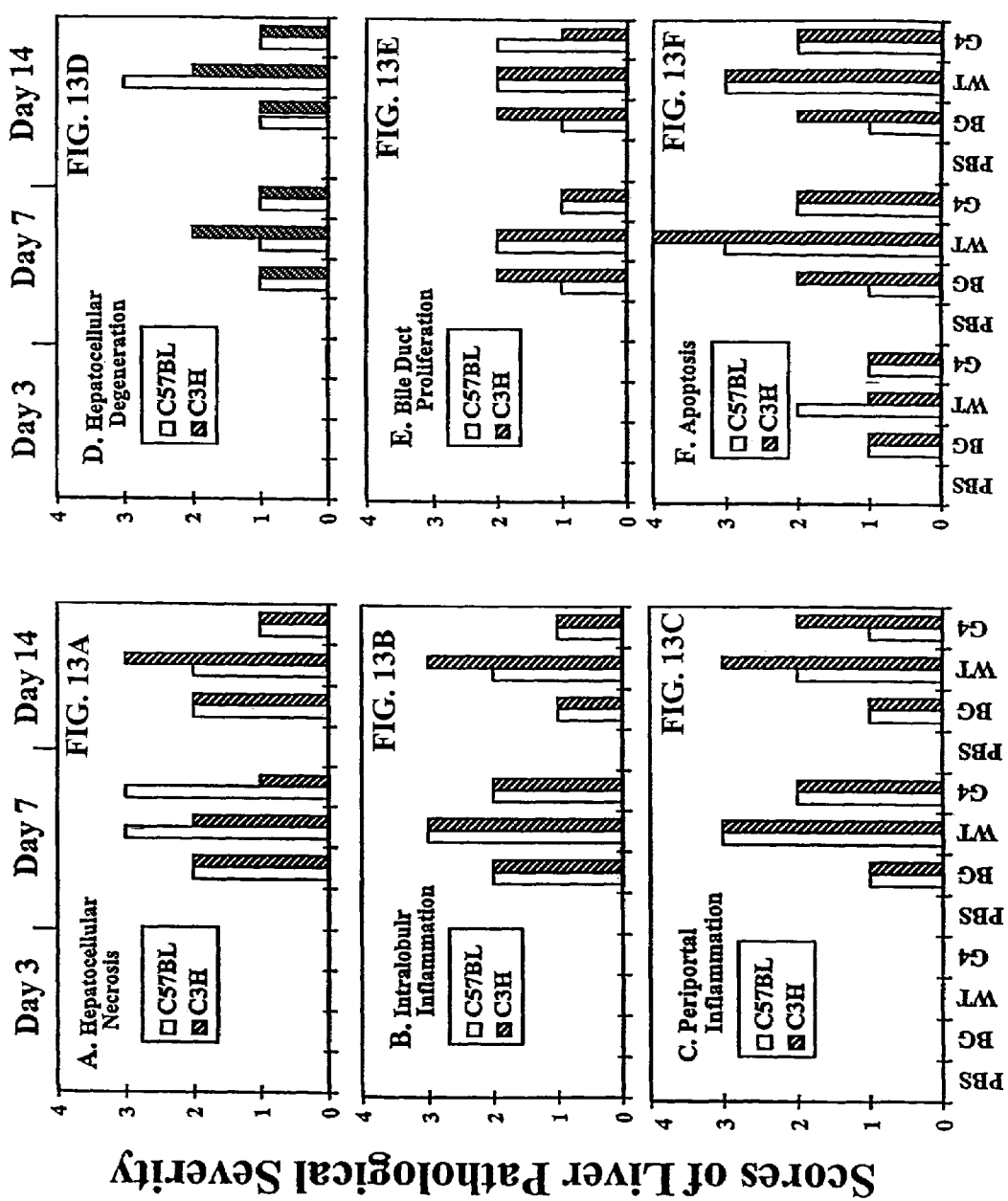

DIMINISHING VIRAL GENE EXPRESSION BY PROMOTER REPLACEMENT

This application is a continuation of application Ser. No. 09/650,946, filed Aug. 29, 2000, now U.S. Pat. No. 6,630,344 which is a continuation of prior application Ser. No. 08/968,014, filed Nov. 12, 1997, now U.S. Pat. No. 6,110,744, which claims the benefit of U.S. Provisional Application No. 60/030,675, filed Nov. 13, 1996. The entire text of the above-referenced applications are specifically incorporated by reference herein without disclaimer.

BACKGROUND OF THE INVENTION

1. Field of the Invention

The present invention relates generally to the field of viral vectors, packaging cell lines, and the use of such viral vectors to express foreign DNA in mammalian cells. The invention also relates to the field of gene therapy, and more specifically to the use of viral vectors to transport genetic material into cells in vivo for therapeutic purposes. More particularly, it concerns viral promoter replacement in order to reduce the expression levels of viral genes in host cells.

2. Description of the Related Art

Gene therapy is an area that offers an attractive approach for the treatment of many diseases and disorders. Many diseases are the result of genetic abnormalities such as gene mutations or deletions, and thus the prospect of replacing a damaged or missing gene with a fully functional gene is provocative. Throughout the last decade, studies of oncogenes and tumor suppressor genes have revealed increasing amounts of evidence that cancer is a disease caused by multiple genetic changes (Chiao et al., 1990; Levine, 1990; Weinberg, 1991; Sugimara et al., 1992). Based on this concept of carcinogenesis, new strategies of therapy have evolved rapidly as alternatives to conventional therapies such as chemo- and radiotherapy (Renan, 1990; Lotze et al., 1992; Pardoll, 1992). One of these strategies is gene therapy, in which tumor suppressor genes, antisense oligonucleotides, and other related genes are used to suppress the growth of malignant cells.

Gene therapy has also been contemplated for transfer of other therapeutically important genes into cells to correct genetic defects. Such genetic defects include deficiencies of adenosine deaminase that result in severe combined immunodeficiency, human blood clotting factor IX in hemophilia B, the dystrophin gene in Duchenne muscular dystrophy, and the cystic fibrosis transmembrane receptor in cystic fibrosis. Gene transfer in these situations requires long term expression of the transgene, and the ability to transfer large DNA fragments, such as the dystrophin cDNA, which is about 14 kB in size.

High efficiency transduction of cells and the ability to administer multiple doses of a therapeutic gene are particularly important points in gene therapy. The ability to transfer a gene into a cell requires a method of transferring the new genetic material across the plasma membrane of the cell and subsequent expression of the gene product to produce an effect on the cell. There are several means to transfer genetic material into a cell, including direct injection, lipofection, transfection of a plasmid, or transduction by a viral vector. The natural ability of viruses to infect a cell and direct gene expression make viral vectors attractive as gene transfer vectors. Other desirable elements of gene transfer vectors include a high transduction efficiency, large capacity for genetic material, targeted gene delivery, tissue-specific gene expression, and the ability to minimize host immunologic responses against the vector.

One particularly gene therapy vector, adenovirus, has been widely studied and well-characterized as a model system for eukaryotic gene expression, and have become the vector of choice for in vivo gene transfer. Adenoviruses are easy to grow and manipulate, and they exhibit broad host range both in vitro and in vivo. They can be produced to high titers, e.g., $10^9$–$10^{11}$ plaque-forming units (PFU)/ml, and they are highly infectious for both dividing and non-dividing cells. The life cycle of adenovirus does not require integration into the host cell genome; the foreign genes encoded by adenovirus vectors are expressed episomally, and therefore have low genotoxicity to the host cells. Adenoviruses are not, however, associated with any significant pathologies. They appear only to be linked to mild forms of disease, and there are no known human malignancies associated with adenovirus infection. Moreover, no side effects have, been reported in studies of vaccination with wild-type adenovirus (Couch et al., 1963; Top et al., 1971), demonstrating their safety and therapeutic potential as in vivo gene transfer vectors.

Many viral vectors have not showed the in vivo results that many have hoped, adenovirus being one of these. Expression levels and duration of expression appear to be two problems. It is thought that one of the causes for these problems is the toxicity and immunogenicity of adenovirus, especially and high dosage.

One way of attaining this goal is to reduce or eliminate the expression of adenoviral proteins in the host. The diminution of viral gene expression and viral replication is desirable for the development of viral vectors used for gene therapy, for attenuated live viral vaccines and for the transformation of cells in vitro for the purpose of protein production. A common approach to this endeavor in the adenoviral system has been to delete certain viral genes. Of course, if the gene is essential to viral replication, the function must be complemented. This complementation is accomplished by providing a "helper" cell line that is transformed with a copy of the deleted viral gene. When this cell is infected, the gene produces its essential product, thereby allowing the virus to replicate. However, in a cell not so transformed, the virus can infect but will not replicate.

Thus, there are many benefits to be obtained by the development of new viral vectors and methods for reducing the viral gene expression of such vectors in host cells.

SUMMARY OF THE INVENTION

The present invention overcomes deficiencies in the prior art by providing new viral vectors and methods for reducing the viral gene expression of such vectors in host cells.

More particularly, the present invention provides a viral vector containing at least one essential viral gene or gene element under the control of an inducible promoter. In preferred embodiments, the inducible promoter is a yeast GAL4 promoter. In particular embodiments of the present invention, the vector is derived from adenovirus and contains an adenoviral origin of replication. In certain other embodiments, the essential viral gene or gene element is selected from the group consisting of E1A, E1B, E2, E4 and E5. As used herein, the term "gene element" may be defined as any DNA sequence that comprises a promoter element operably linked to a piece of DNA that encodes a polypeptide or protein product.

In certain embodiments, a viral vector is provided, wherein at least one viral gene or gene element is deleted therefrom. In such aspects of the invention, the deleted viral gene or gene element is selected from the group consisting E1A, E1B, E2, E3, E4 and E5, and the essential viral gene or gene element and the deleted viral gene and gene element are different. In certain embodiments, the E2 gene also is under the control of an inducible promoter. In other embodiments, the E5 gene also is under the control of an inducible promoter. In some embodiments, it is contemplated that at least two viral genes or gene elements are deleted. In particular embodiments the deleted genes may be E1A and E1B. In other aspects it is contemplated that the E3 gene also is deleted.

In particular embodiments there is provided a viral vector wherein the essential viral gene or gene element is E4. Other embodiments of the invention provide a viral vector containing at least one essential gene or gene element under the control of an inducible promoter, wherein the inducible promoter is selected from the group consisting of the auxin inducible promoter, tet-responsive element and an ecdysone hybrid response element. It is contemplated that a viral vector may further comprise a heterologous gene. In these aspects the heterologous gene is under the control of a promoter active in eukaryotic cells. In particular embodiments the promoter may be CMV promoter.

In certain embodiments the viral vector of the present invention further comprises a polyadenylation signal in operable relation to the heterologous gene. In particular aspects of the present invention the polyadenylation signal is selected from the group consisting of adenovirus, SV40 and bovine growth hormone. In certain embodiments the heterologous gene is selected from the group consisting of a tumor suppressor, an antisense transcript, a vaccine antigen and a single-chain antibody. In certain embodiments of the present invention the tumor suppressor is selected from the group consisting of but not limited to p53, RB, APC, DCC, NF-1, NF-2, WT-1, MEN-I, MEN-II, BRCA1, VHL, FCC, MCC, MMAC1, zac1, p16, p21, p57, p73, p27, C-CAM and BRAC2. In other embodiments, the antisense transcript may comprise antisense against oncogenes such as, for example, ras, myc, neu, raf, erb, src, fms, jun, trk, ret, gsp, hst, bcl and abl. The heterologous gene, in alternative embodiments, may encode an inducer of apoptosis, such as Bax, Bak, Bcl-$X_s$, Bik, Bid, Harakiri, Ad E1B, Bad and ICE-CED3 proteases.

Other aspects of the present invention provide a cell comprising a heterologous gene encoding at least a first factor that induces a promoter that is capable of activity in eukaryotic cells. In particular embodiments the first factor is a fusion polypeptide of VP16 and a fusion partner, the term "fusion partner" refers to a polypeptide that may bind to an element within a promoter region. As used herein the term "fusion protein" or "fusion polypeptide" is a protein or polypeptide encoded by two fused genes or gene elements. In particular embodiments the fusion partner for VP16 is selected from the group consisting of GAL4, tet repressor, ecdysone receptor and auxin. In other embodiments the factor is a fusion polypeptide of the estrogen receptor hormone binding domain and a fusion partner. In such embodiments, the fusion partner for estrogen receptor hormone binding domain is selected from the group consisting of GAL4, tet repressor/VP16 fusion protein, ecdysone receptor and auxin. In further embodiments the GAL4 fused to VP16.

The cell may further comprise at least one viral gene or gene element essential to the replication of the corresponding virus. In preferred aspects the viral gene or gene element is an adenoviral gene selected from the group consisting of E1A, E1B, E2, E4 and E5. In certain embodiments the adenoviral gene is E1B. In other embodiments the adenoviral gene further comprises the E1A gene. In specific embodiments the adenoviral gene further comprises the E2 gene. In other embodiments it is envisioned that the adenoviral gene is E1A.

In preferred embodiments, the cell further comprises a gene encoding at least at second factor that induces a promoter that is capable of activity in eukaryotic cells. In one embodiment the second factor is a fusion polypeptide of VP16 and a fusion partner. In another embodiment, the second factor is a fusion polypeptide of the estrogen receptor and a fusion partner.

Also provided by the present invention are methods for producing an infectious, conditionally replication-defective viral particles comprising providing a cell comprising a heterologous gene encoding at least a first factor that induces a promoter that is capable of activity in eukaryotic cells, contacting the cell with a viral vector, the viral vector comprising at least one essential viral gene or gene element under the control of a promoter that is induced by the first factor and inactive in the absence of the factor, culturing the cell under conditions permitting the uptake of the viral vector by, and replication in, the cell; and harvesting infectious virus particles produced by the cell.

In specific embodiments the cell further comprises an essential viral gene or gene element and the vector lacks a functional copy of the essential viral gene. In other embodiments the viral vector comprises a heterologous gene. In preferred embodiments the viral vector is derived from adenovirus and contains an adenoviral origin of replication.

The present invention also provides a method for producing a protein in a cell comprising contacting the cell with an infectious viral particle, the particle comprising a viral vector comprising at least one essential viral gene or gene element under the control of a promoter that is induced by the first factor and inactive in the absence of the factor and a heterologous gene, and culturing the cell under conditions permitting the uptake of the particle by the cell and the synthesis of the product of the heterologous gene in the cell, the conditions not including the first factor. In preferred embodiment the method further comprises the step of isolating the product. In other preferred embodiments the viral vector is derived from adenovirus and contains an adenoviral origin of replication.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2A, FIG. 2B and FIG. 2C. Construction and characterization of adenoviral vectors containing RSV-hFIX. FIG. 2A. Schematics of the two plasmids used to construct adenoviral vectors whose E4 promoter was replaced by GAL4/TATA. The open bars represent adenoviral sequences; the numbers indicate the corresponding positions in the viral genome. Filled areas represent a minimal promoter consisting of five consensus 17-mer GAL4-binding sites upstream from the adenovirus E1B TATA box. FIG. 2B. Schematics of the three recombinant adenoviral constructs containing the RSV-hFIX (RSV-hF9) expression cassette. The expression cassette, containing a Rous sarcoma virus-long terminal repeat (RSV-LTR), hFIX cDNA, and a bovine growth hormone polyadenylation signal sequence in a right-to-left orientation, was placed in the adenoviral E1 region. AdE4A/RSV-hFIX and AdE4B/RSV-hFIX were constructed using pBF7A and pBF7B, respectively, which differ in the lengths of their right-end terminal fragments. Filled boxes represent the GAL4/TATA promoter. FIG. 2C. PCR™ analysis of E4 region. DNA isolated from purified adenoviruses was used as template for PCR™ with primers amplifying adenoviral sequences from 35460 to 35935. The PCR™ products were run on 2% agarose gels. Lane 1, 100-bp ladders; lanes 2, 6 wild-type adenovirus; lanes 3, 7, Ad/RSV-hFIX; lanes 4, 8, AdE4A/RSV-hFIX; lanes 5, 9, AdE4B/RSV-hFIX. Lanes 6-9, PCR™ products digested with SphI.

FIG. 3A, FIG. 3B, FIG. 3C and FIG. 3D. Propagation of adenoviral vectors in various cell lines. Virus production was measured in: FIG. 3A 293 cells at MOI=2; FIG. 3B 293/GV16 cells at MOI=2; FIG. 3C H1299 cells at MOI=10; and FIG. 3D H1299 cells at MOI=100. The infectious units recovered were determined by $TCID_{50}$ assay and presented either as infectious units/cell (from 293 or 293/GV16 cells) or as total infectious units ($\log_{10}$)/$10^6$ cells (from H1299 cells). The values represent the mean of duplicate assays. Open circles=Ad/RSV-hFIX; open triangles=AdE4A/RSV-hFIX; open squares=AdE4B/RSV-hFIX.

FIG. 8A, FIG. 8B, FIG. 8C, FIG. 8D, FIG. 8E, FIG. 8F, FIG. 8G and FIG. 8H. In vivo evaluation of GAL4/TATA promoter activity. Adult Balb/c mice 3/group were infused with $1 \times 10^9$ pfu of virus as indicated at the bottom of the graphs. The luciferase activities were expressed as light units/μg of cellular. Luciferase activities were readily detected in liver (FIG. 8A), lung (FIG. 8B), kidney (FIG. 8C), spleen (FIG. 8D), ovary (FIG. 8E), intestine (FIG. 8F), heart (FIG. 8G), and brain (FIG. 8H) of mice infused with Ad/RSV-Luc. No or only background levels of luciferase activities were detected in all organs tested in animals infused with other viral constructs, including those infused with Ad/GT-Luc.

FIG. 9A and FIG. 9B. Southern blot analysis of viral DNA in recombinant adenovirus-infected H1299 cells at MOI 80. FIG. 9A shows the cellular DNA was isolated from adenovirus-transfected H 1299 cells at indicated time postinfection. 5 μg of DNA was digested with BamHI and fractionated on a 1% agarose gel. The viral DNA was detected using $^{32}$p-labeled E4orf6 DNA fragment (750 bp) as a probe. CK, the negative control with PBS; AD, the positive control with adenovirus DNA. FIG. 9B shows the quantification of the viral DNA bands on the southern blot of FIG. 9A. Images were generated and analyzed using a Phosphoimage Analysis System.

FIG. 10A and FIG. 10B show blots for viral hexon protein in H1299 and A549 cells respectively; FIG. 10C shows blots for human p53 in H1299. The viral constructs and d postinfection were indicated above and below each blot, respectively. CK, the negative control with PBS.

FIG. 11A and FIG. 11B shows the effect on cell growth of H1299 and A549 cells, respectively. The growth rate was calculated as percentage of the PBS-treated control cells. FIG. 11C shows the effect on apoptosis of H1299 and A549 cells. Apoptosis was analyzed by flow cytometry using TUNEL reaction with FITC-labeled dUTP. CK, the negative control with PBS.

FIG. 12A, FIG. 12B, FIG. 12C, and FIG. 12D Evaluation of toxicity in recombinant adenovirus-injected mouse livers by SGOT and SGPT analysis. Five animals were used for each treatment group. Each animal was injected with 100 μl of $1 \times 10^{10}$ pfu virus through tail veil using PBS as mock control. Blood samples were collected from mouse tail for SGOT or SGPT assay at d postinjection as indicated.

FIG. 13A, FIG. 13B, FIG. 13C, FIG. 13D, FIG. 13E, and FIG. 13F Histopathology of mouse livers in response to recombinant adenoviruses. Severity of pathological features were scored as 0 for no significant lesions observed; 1 for mild; 2 for moderate;, 3 for marked and 4 for severe.

FIG. 14A and FIG. 14B CTL responses to recombinant adenoviruses in mice after I.V. inoculations. CTL responses in C3H mice and syngeneic 1422 cell line as target (FIG. 14A); CTL responses in C57BL mice and syngeneic CL4/SV40 as target (FIG. 14B).

DESCRIPTION OF ILLUSTRATIVE EMBODIMENTS

Figure 1:
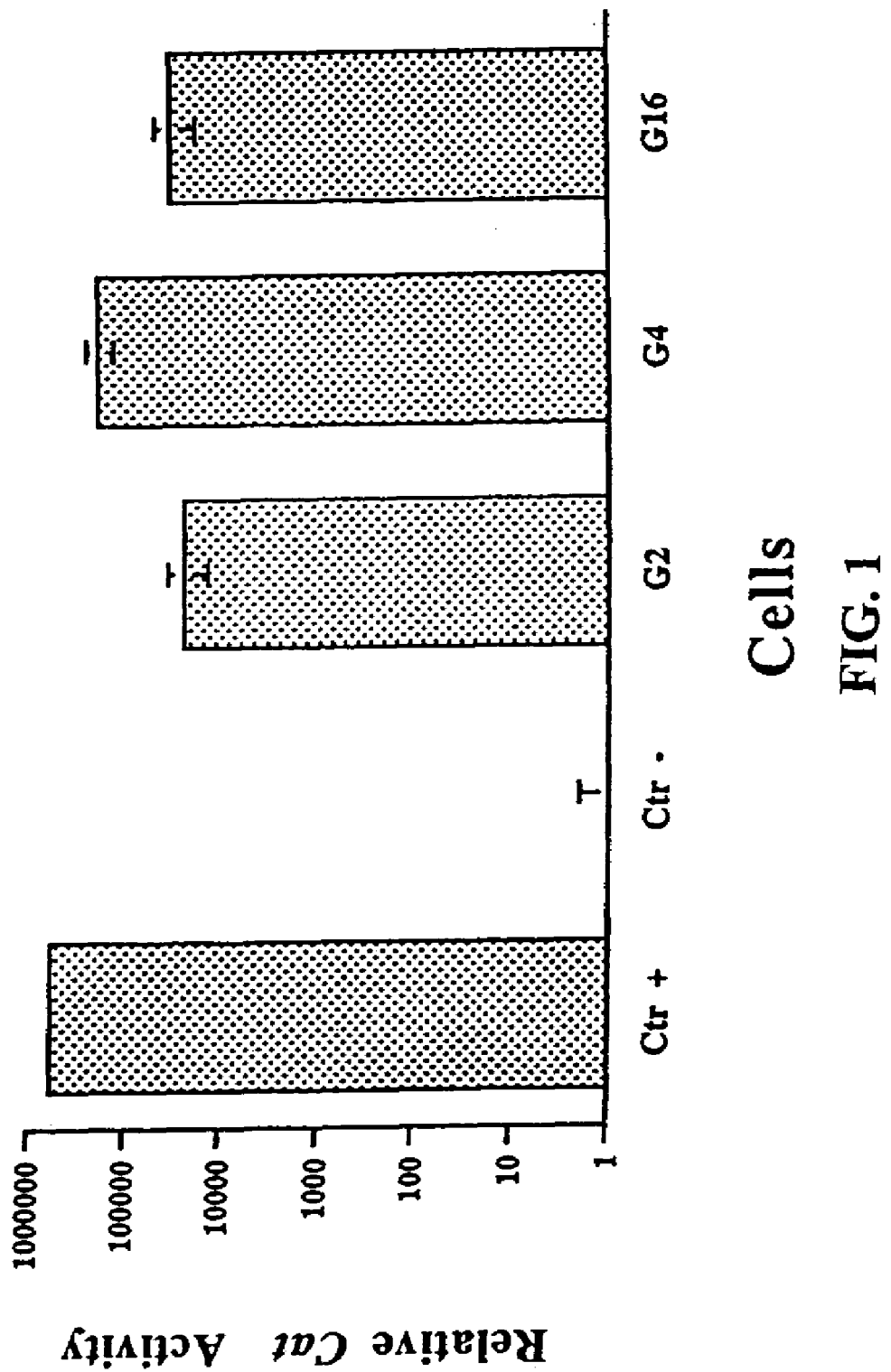
FIG. 1. Selection of 293 cells transformed with the gene encoding GAL4/VP16 fusion protein. 293 cells from single colonies were plated in 6-well plates at 1×10/well. The cells were transduced with 6 μg of pG5EC and 1 μg of pRSV/LacZ. Parental 293 cells were used as negative controls (Ctr−). 293 cells transduced with 100 ng of pM2VP16 in addition to PG5EC and pRSV/LacZ were used as positive controls (Ctr+). Cell extracts (50 μg of protein) were used for CAT and β-galactosidase assays. CAT activity was expressed as yield of product in 20 min. Values for both CAT and β-galactosidase activity were determined at the same time. Each value represents mean±s.d. of three assays.

Gene transfer generally involves three principal elements: therapeutic genes, delivery systems, and target cells. A particular challenge of current gene transfer protocols is the attaining and maintenance of high expression levels of transgenes in host cells. One attempt to achieve this goal is via the reduction of toxic and immunologic responses against the vector-associated antigens. In vitro, the cell may die or produce lower levels of protein due to the toxic effects of some viral gene expression. In immunocompetent individuals, the therapeutic efficacy of gene transfer may be reduced because of an existing or induced immune response. In cases where repeated injections of a gene therapy vector is necessary, for example in cancer, patients may over time develop strong immune responses against the vector that may severely reduce its therapeutic efficacy.

Indeed, recent studies have indicated that the limited in vivo persistence of transgene expression is most likely the result of host immune responses against virally infected target cells (Dai et al., 1995; Englehardt et al., 1994; Yang et al., 1994). In addition, the outer structural proteins of adenovirus vectors are high immunogenic; potent humoral and cellular responses develop soon after administration of the vector, particularly when the vector is administered intravenously. Thus the host can reduce the therapeutic effect of the gene transfer vector by neutralizing the virus even before it infects the target cell or by eliminating cells transduced by the vector and expressing viral proteins. Such an immune response can dramatically reduce the efficacy of repeated administration of vector.

Studies in immune compromised animals has shown that the viral genome can be stably maintained in an episomal form in excess of 12 months (Dai et al., 1995; Yang et al., 1995). Clearly, the host immune response against free viral particles and cells infected by the virus is the most significant obstacle to long term gene expression mediated by adenovirus vectors. The present invention represents a novel strategy to reduce the level of expression of adenoviral gene products in adenovirus gene transfer vectors, with the end result being reduced immunogenicity and cellular toxicity of the viral gene products, while at the same time prolonging transgene expression. These attributes make this vector particularly useful for gene transfer. Importantly, the likelihood of producing replication competent virus would also be significantly reduced by the diminished viral DNA replication, thus further increasing the safety of the vector for in vivo use.

Thus, according to the present invention, viral vectors are prepared using a "promoter-replacement" strategy in which various viral genes required for replication are placed under the control of an inducible promoter. The virus is propagated in a host cell that expresses an inducing factor, thereby permitting synthesis of the essential gene product and the replication of the viral vector.

In certain embodiments of the present invention, the viral vectors described herein are used in the transforming of cells in vitro for producing foreign proteins. In addition, the viral vectors may be used in gene therapeutic contexts for the provision of therapeutic genes to cells in ex vivo and in vivo contexts. Finally, it is contemplated that viral vectors of the present invention will find use as attenuated live virus vaccine vectors. It is envisioned that a vector made according to the present invention will provide efficient, high level and long term expression of a transgene when introduced into a host cell.

A. Immune Response to Vector Antigens

Most viral infections in immune competent mammals result in a cell-mediated immune response against the virus infected cells, the net effect being lysis of the cells. During viral infections, viral proteins are synthesized in the cell for inclusion into new viral particles. Some of those endogenous viral proteins are also degraded and transported into the class I antigen presentation pathway, where the foreign antigens associate with a class I MHC molecule. This peptide-MHC complex is then transported to the surface of the cells where the foreign peptide is presented, in the context of self MHC, to cytotoxic T cells (CTLs). Upon recognition of the antigen as foreign, the CTLs lyse the target cell either through molecular interactions that induce apoptosis, or secretion of pore forming enzymes that poke holes in the plasma membrane disrupting its integrity. Thus the CTL-mediated immune response plays a significant role in the clearance of virally infected cells.

Diminishing a viral gene's expression, therefore, can help reduce the immune response of the host to viral gene products. It also can disable viral replication and spread in vivo, resulting in a limited infection that cannot be transmitted. In addition, inactivation of cytotoxic genes can reduce the virulence of the virus thereby generating an attenuated virus that may be useful as a live virus vector. A final benefit is increased the safety of the viral vector thereby allowing higher doses of the virus to be used to attain the desired biological or therapeutic effects. Overall, the net result of reducing viral gene expression is a higher therapeutic index.

Identifying and eliminating the targets of the immune response against replication-incompetent adenovirus vectors is critical to the long term gene expression from adenovirus-mediated gene transfer. In an infection with wild-type adenovirus, the major antigens presented by class I MHC molecules originate from the E1A gene products, and to a lesser extent, the E2 and later gene products (Mullbacher et al., 1989; Urbanelli et al., 1989). Fortunately, most of the current adenovirus vectors used for gene transfer have been made replication defective by deleting the E1 region, which encodes E1A and E1B genes of adenovirus.

However, other adenoviral early gene products also are involved in the regulation of replication and late gene expression. Infection of cells with adenoviral vectors containing an E1 region deletion and a temperature sensitive mutation for the E2A-encoded DNA binding protein persist longer that vectors with an E1 deletion alone (Engelhardt et al., 1994). The E4 gene encodes proteins that are important for viral replication, which is required for expression of late gene products, such as adenoviral structural proteins. Therefore, as with most viral infections, intracellular expression of viral gene products leads to the presentation of the viral antigens by class I MHC molecules to the host cellular immune system.

Interestingly, the adenoviral E3 gene encodes an endoplasmic reticulum transmembrane protein that binds host class I MHC antigens, providing a virally-mediated block to antigen presentation and subsequent lysis of the target cell by cytotoxic T lymphocytes. Studies in animal models have also shown that the 19K transcript of E3 acts as an anti-inflammatory and immunosuppressive factor. Although low levels of E3 transcripts would be expected in E1A deleted vectors, in certain cell types such as lymphocytes, the relative levels of the 19K transcript is similar to that in cells that have the E1A protein (Korner and Burgert, 1994). Thus adenoviral vectors, that contain a functional E3 gene might actually aid in the suppression of host cellular immune responses. Conversely, since the E3 proteins would be foreign to the host cell, the E3 proteins themselves would be immunogenic. In addition, since the E3 region of adenovirus is not required for viral replication, it may be deleted in adenoviral vectors used for gene transfer, thus increasing the available space for insertion of heterologous DNA sequences, heterologous gene sequences being defined as not naturally occurring in the context of that cell or vector.

Although current adenovirus vectors used in gene therapy are replication-incompetent because of E1 region deletions, and therefore large amounts of viral proteins are not produced, low levels of viral proteins are still observed. One reason for this may be that cellular factors that are similar to the E1 gene products may be able to transactivate gene expression in certain cell types. In addition, it has been noted that cells that have been treated with a high multiplicity of infection, the E1 deleted adenovirus can still replicate at low levels (Jones et al., 1979).

B. Reducing Viral Gene Expression

Mutagenesis of viral genes can be achieved quite readily with various reagents and protocols. Viral mutants can be selected in accordance with changes n growth properties, such as host range restrictions or temperature sensitivity (Ensinger and Ginsberg, 1972; Fenner, 1974). Random mutagenesis, however, can result in the accumulation of many mutations, making it difficult to define their genetic basis. A well-characterized mutation can be used effectively to limit gene expression (Englehardt et al., 1994; Yang et al., 1994), but this strategy is limited through the availability of such a mutation.

There are other mechanisms to avoid or suppress the immune response to adenovirus vectors. Direct immunosuppression of the patient's immune system with drugs like cyclosporin, or FK506 (Vilquin et al., 1995), for example, can be accomplished readily and is well known in the art. Similarly, depletion of specific immune system cells may also prolong transgene expression from gene therapy vectors (Kolls et al., 1996). However, the obvious drawbacks to these approaches is that the patient becomes susceptible to other, potentially more threatening, bacterial or viral infections. In addition, some candidate gene therapy patients, such as those with cancer or adenosine deaminase deficiency, are already quite sick because of their disease or the therapy used to treat the disease, and further reduction in the efficacy of their immune system could open them up to further complications. As a result, these approaches are better suited to complementing other methods of reducing immunogenicity, as discussed below, rather than means in and of themselves.

Gene deletion can be used to reduce the expression of viral genes, and thus lower the vector-associated toxicity and availability of immunologically reactive antigens. Indeed, the current adenovirus gene transfer vectors are replication-incompetent and have reduced expression of most adenoviral gene products because of gene deletions. However, the required functions of the deleted genes must be supplied in trans for viral propagation; and therefore, a packaging cell line transformed with the deleted gene or genes is usually required for efficient viral propagation (Graham et al., 1977; Weinberg and Ketner, 1983; Wang et al., 1995; Gorziglia et al., 1996) Unfortunately, establishing a cell line that expresses several viral genes usually proves to be a most difficult and time-consuming task because some of the viral genes are often toxic to host cells.

The present invention provides a new and improved method of reducing the expression of viral genes in a therapeutic vector. Through the use of a synthetic promoter linked to viral genes, a gene transfer vector has been designed in which the expression of viral genes can be tightly controlled. The expression of viral genes required for replication, i.e., "essential" genes, is allowed only in producer or helper cells that express an appropriate transactivating polypeptide. Thus, the virus can only replicate in the producer cells and not in any other type of cell, including host cells. In adenovirus, late gene expression depends on viral DNA replication. Therefore, a reduction in the viral replication of the vector eliminates or greatly reduces the expression of adenoviral gene products. Diminished viral gene expression ultimately results in a decreased immune response against the transduced cell, and allows persistent expression of the transgene, resulting in a higher therapeutic index.

The present invention further reduces the levels of viral gene expression, particularly late viral gene expression, through promoter replacement. Enhancers and promoters that regulate the transcription of viral genes in cell-, tissue- or disease-specific fashion are often major determinants of viral tropism. Replacing a gene's promoter may allow the gene's expression to be controlled. Expression of viral genes in packaging cells but not in vivo in humans can be achieved through the replacement of a gene's promoter with an "inducible" or synthetic promoter, defined a being active only in the packaging cell line that contains a specific transactivating protein. In such a system, the promoter should (i) have no or very low levels of transcriptional activity in the absence of transactivating proteins that are normally absent in mammalian cells and (ii) sufficiently promote viral production in the presence of the specific transactivating protein when expressed in the packaging cells.

The present inventors have exemplified this approach to reduce the levels of adenoviral E4 gene products. The E4 gene encodes proteins with several different functions including mediating transcriptional regulation, mRNA transport, and DNA replication. E4 gene expression is normally dependent on the E1A gene product, so with current adenovirus gene transfer vectors, there are already only low levels of E4 transcripts produced. However, it has been reported that even in the absence of E1A, certain E4 transcripts are produced. Further reducing the in vivo expression of E4 gene products will result in decreased chances of viral replication, even at high MOI. Transcription from the major late promoter of late adenoviral genes is dependent on both a virally encoded transcription factor and viral DNA molecules, thus decreased DNA replication results in drastically reduced levels of late gene products. Overall, the net effect is lower levels of potentially immunoreactive antigens, which should increase the therapeutic index of gene transfer. Importantly, the incidence of forming replication competent adenoviral particles will be greatly reduced, making these vectors even more safe for in vivo use.

The promoter region of adenovirus E4 has been replaced, in the present invention, with a synthetic promoter composed of a minimal TATA box and five consensus 17-mer GAL4-binding site elements (GAL4/TATA). Since most mammalian cells express no GAL4-like activity, a synthetic GAL4-responsive promoter containing GAL4-binding sites and a TATA box should have no or extremely low basal activity in the absence of a GAL4 transactivator, and high activity in its presence. GAL4 is a transcriptional activator derived from yeast, that when fused to a highly acidic portion of the herpes simplex virus protein VP16, is a very potent activator of transcription (Sadowski et al., 1988). Thus, genes that have GAL4 binding sites in their promoter regions, are highly activated by the introduction of the GAL4-VP16 fusion protein.

The present adenoviral vector was constructed by replacement of the E4 promoter with GAL4/TATA in the original E4 location (see Example 3). Transfer plasmids were constructed that contained adenoviral E4 sequences and the GAL4/TATA promoter region. A shuttle vector consisting of the adenovirus type 5 backbone into which a human factor IX transgene driven by the RSV-LTR was inserted into the E1 region was used to supply the adenoviral E4 region. Recombinant adenoviruses containing the RSV promoter-driven human factor IX cDNA and adenovirus E4 gene driven by the GAL4/TATA promoter were constructed by cotransfection of the transfer plasmids with a fragment containing human factor IX transgene into producer cells. The resulting recombinant adenoviruses obtained by homologous recombination, when transduced into non-producer cells, maintain high levels of transgene expression while at the same time exhibit low levels of adenoviral gene expression (Table 3 and FIG. 5 and FIG. 6).

It is further envisioned that other combinations of transcriptional activators and promoters could be used in a similar manner to activate transcription only in the presence of the transactivator, thus producing viral particles in appropriate producer cells. GAL4 alone could also be provided in trans to effect transcription of the desired gene driven by a GAL4/TATA promoter (Brand and Perrimon, 1993).

Another transcriptional activator that could be used in a similar manner is a GAL4-estrogen receptor fusion protein (GAL4-ER), where the GAL4 protein is fused to the hormone binding region of the human estrogen receptor (Braselmann et al., 1993). It is envisioned that the VP16 protein could also be added to this complex to render the complex more potent and less cell type restricted, as compared to GAL4-ER alone. The estrogen receptor targets the estrogen response element and thus can be used as an independent regulator of transcription initiation.

Yet another system that could be used according to the present invention utilizes a synthetic hormone. In this system a vector with a promoter is operably linked to a gene whose expression is to be regulated. The promoter could consist of a DNA binding domain, an activation domain, and a ligand binding domain operably linked together. At least one of these components would not naturally be found in humans. An example of each of these components would be the GAL4 binding domain, the HSV-VP16 transactivating domain, and a steroid receptor binding domain, respectively. To initiate transcription of the gene, the vector would be transduced into producer cells that express an initiation complex consisting of a DNA binding protein (e.g., GAL4), a transactivating protein (e.g., VP16), and a ligand receptor (e.g., steroid receptor). In the presence of a steroid capable of binding to the steroid receptor, a conformational change is induced such that the complex could now bind the promoter region and initiate transcription of the gene. In this example, since the GAL4 protein is not present in normal mammalian cells, transduction of this vector into mammalian cells would not result in expression of the controlled gene, which is the desired effect. The presence of the steroid receptor binding domain would allow for the selective expression of the gene only when the steroid is present, thus giving control over when to turn on and off expression of the gene in producer cells.

Other transcriptional activator/promoter combinations that could be used include a tetracycline-responsive transcriptional activator/tet-responsive element system (Clonetech, Palo Alto, Calif.) which consists of the VP16 transactivation domain fused to a bacterial tet repressor, such that upon addition of tetracycline or tetracycline derivatives, the fusion protein can bind to the tet-responsive element and activate transcription.

Another similar system that could be used according to the present invention utilizes the plant hormone auxin. In this system, an auxin-responsive promoter element or elements is operably linked to a gene to be regulated, for example the adenoviral E4 gene, in an adenoviral vector. In the presence of auxin, which would only be present in producer cells, transcription would be initiated from the auxin promoter to express the E4 gene, thus allowing viral replication to proceed. Therefore, upon transduction of the progeny virus into normal mammalian cells that do not naturally express the auxin transactivating protein, no E4 proteins would be made.

Yet another system that works on similar principles is the Ecdysone system (Invitrogen, San Diego, Calif.), which consists of a ecdysone receptor from fruit flies that is co-expressed with VP16. Upon induction with muristerone, a glucocorticoid, the ecdysone receptor combines with VP16 and activates transcription from a hybrid response element upstream of the target gene. Similar systems that provide for the transactivation of gene expression for the production of adenoviral particles in packaging cells, but not in cells lacking the transactivating proteins are contemplated herein.

C. Cell Lines

In another embodiment of the present invention, a cell line is employed that is capable of supporting the replication of a recombinant adenovirus vectors having defects in certain adenoviral genes. This cell line is also called a helper, or producer cell line because of the ability to provide in trans the necessary elements for replication of the defective adenovirus. The prototype for an adenoviral helper cell is the 293 cell line, which has been transformed with the gene products of the E1 region of adenovirus. These cells support the replication of adenoviral vectors lacking E1 gene functions by providing in trans the proteins encoded by the E1 region, and thus enable replication of the virus. According to the present invention, a helper cell line also will contain a gene encoding a transactivating or inducing factor that will stimulate expression of a cognate inducible promoter in the viral vector.

According to the present invention, helper cells are derived from a mammalian cell and, preferably, from a primate cell such as a human embryonic kidney cell. Although various primate cells are preferred, and human or even human embryonic kidney cells are most preferred, any type of cell that is capable of supporting replication of the adenovirus or adenoviral vector would be acceptable in the practice of the invention. Other cell types might include, but are not limited to, Vero cells, Chinese hamster ovary cells or any eukaryotic cell for which tissue culture protocols are established as long as the cell is permissive for the growth of adenovirus. The phrase "permissive for the growth of adenovirus" is means that the adenovirus or adenoviral vector is able to complete the entire intracellular life cycle and produce mature infectious adenovirus particles within the cellular environment.

The helper cell line may be derived from an existing cell line such as 293 cells, or developed de novo, as discussed further, below, in the section on gene transfer. Such helper cells will express the adenoviral proteins and transactivating proteins necessary to support the growth of otherwise replication-incompetent adenoviruses according to the present invention. A preferred helper cell line is any cell that expresses the adenoviral E1 region gene products as well as the GAL4/VP16 transactivating protein and is adenovirus permissive. Other suitable systems for incorporation into host cells are described in the preceding section. A most preferred helper cell line is the 293 cell line that expresses the GAL4/VP16 fusion protein. The inventors have created such a helper cell line (GV16) by transfecting 293 cells with a plasmid containing an SV40 early promoter-driven gene that encodes the GAL4/VP16 fusion protein. This helper cell line, when transduced with an adenoviral vector lacking the E1 region and whose E4 gene promoter consists of the GAL4/TATA sequence, supports the replication of the adenoviral vector and this produces progeny virus (see Example 4). The progeny virus remain replication-defective when introduced into non-helper cells, however, and will not produce significant levels of viral proteins.

Cells may be screened for their ability to support viral replication of a vector according to the present invention following their generation by contacting a layer of uninfected cells with virus particles, followed by incubation of the cells under conditions for optimal viral growth. The formation of viral plaques, or cell-free areas in the cell layer, is the result of cell lysis caused by the expression of certain viral products. Generalized CPE or screening for expression of viral antigens also may be utilized.

Cells may include combinations having the adenoviral genes E1A and E1B and E2, E1A and E1B and E4, E1A and E1B and E5, E1A and E1B and E2 and E4, E1A and E1B and E2 and E5, and E1A and E1B and E4 and E5. E3 can be deleted from any of the vectors, but need not be contained in a corresponding cell line as it is non-essential. Of course, these genes will be in the context of a cell that already contains at least one of the transactivating or inducing factors discussed elsewhere in this document.

D. Viral Vectors

Although the present invention is exemplified with adenovirus, it is contemplated that a variety of viral particles may be employed according to the present invention. To determine whether other viral vectors could be manipulated in this manner, one of skill in the art can perform simple molecular biology techniques and assays. For example, replacement of promoter elements can be achieved through various cloning techniques well known in the art. Assays for the detection of gene expression such as Northern or Western blots can then be used to determine expression levels of the viral gene products in various cell types, either in vitro, or in vivo, through the use of biopsies. Similarly, techniques to measure both the humoral and cell-mediated immune response to antigens are well known in the art and include enzyme-linked immunosorbent assays (ELISA), cytotoxic T Lymphocyte (CTL) assays and natural killer cell assays. In vitro infectivity assays also measure cytotoxic or cytopathic effects. Alternatively, viral vectors with a marker gene, such as β-galactosidase or luciferase as the transgene, can be employed. Measurement of the expression of the marker gene can then be done either qualitatively (e.g., microscopically) or quantitatively (e.g., flow cytometrically).

i) Adenovirus

Adenovirus is particularly suitable for use as a gene transfer vector because of its mid-sized DNA genome, ease of manipulation, high titer, broad target cell range, and high infectivity. Adenovirus vectors have been successfully used in eukaryotic gene expression (Levrero et al., 1991; Gomex-Foix et al., 1992) and vaccine development (Grunhaus and Horwitz, 1992; Graham and Prevec, 1991). Recently, animal studies demonstrated that recombinant adenovirus could be used for gene therapy (Stratford-Perricaudet, 1992; Stratford-Perricaudet et al., 1990; Rich et al., 1993). Successful studies in administering recombinant adenoviruses to different tissues include tracheal instillation to airway and lung epithelium (Rosenfeld et al., 1991; Rosenfeld et al., 1992), muscle injection (Ragot et al., 1993), peripheral intravenous injection (Hertz and Gerard, 1993), stereotactic inoculation into the brain (Le Gal La Salle et al., 1993), transduction into cardiac muscle cells (Kass-Eisler et al., 1993), and inoculation of the retina (Bennett et al., 1994).

The genetic makeup of the adenoviral genome can be readily modified to make an optimal gene therapy vector. One way to optimize the vector is to maximize the heterologous DNA carrying capacity of the vector which can be accomplished by providing some of the required adenoviral gene products by helper cells or helper viruses.

The roughly 36 kB viral genome is bound by 100–200 base pair inverted terminal repeats (ITR), within which are contained cis-acting elements for viral DNA replication and packaging. The transcription of early (E) and late (L) regions of the genome are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off (Renan, 1990). The products of the late genes (L1, L2, L3, L4 and L5), including the majority of the viral capsid proteins, are expressed only after significant processing of a single primary transcript issued by the major late promoter (MLP). The MLP (located at 16.8 map units) is particularly efficient during the late phase of infection, and all the mRNAs issued by this promoter possess a 5' tripartite leader (TL) sequence which makes them preferred mRNAs for translation. Also essential to the construct is a viral origin of replication.

It is possible to remove large portions of the adenoviral genome and provide the gene products in trans because the cis elements required for viral DNA replication all are located within the ITRs at either end of the viral genome. Thus, inclusion of these elements in a plasmid or stably integrated into the producer cell genome should allow replication in the presence of a non-defective adenovirus (Hay et al., 1984). The only other viral element required to be provided in cis is the packaging signal for viral encapsidation, located between 194–385 bp (0.5–1.1 map units) at the left end of the viral genome (Hearing et al., 1987). This signal is similar to the protein recognition site in bacteriophage 1 DNA where a specific sequence close to the left end, but outside the cohesive end sequence, mediates the binding of proteins that are required for insertion of the DNA into the head structure. It has been shown that E1 substitution vectors of adenovirus with a 450 bp (0–1.25 map units)

fragment at the left end of the viral genome is sufficient to direct viral DNA packaging in 293 cells (Levrero et al., 1991).

The current generation of adenovirus vectors contain deletions in the E1 region, and the replication of these defective vectors is supported by packaging cell lines such as 293 cells that provide the E1 region gene products. Similarly, adenovirus vectors with the E1 and E4 gene deleted, but provided by 293 cells expressing both viral gene products, have been made. It is possible to make even larger deletions on the adenovirus genome and then provide the deleted genes in trans, either by a helper virus or helper cell, or both.

The ability to selectively reduce the level of viral gene expression also makes adenovirus desirable as a gene transfer vector. The complete removal of these adenoviral genes would obviously eliminate the host immune response, however, it can be difficult to establish packaging cell lines because of viral gene-mediated toxicity. The present invention, through the replacement of viral promoter elements with a synthetic promoter, significantly reduces the level of viral gene expression.

The present invention contemplates the reduction of a variety of genes in adenovirus. It is envisioned that preferred adenoviral vectors used for gene transfer will have at least i) a deletion of the E1B and/or E1A region and ii) an inducible or synthetic promoter according to the present invention substituted for the normal viral promoter that regulates expression of one or more of the early adenoviral genes E2, E3, E4 and E5. Similarly, a synthetic promoter could be substituted for the adenoviral major late promoter, which regulates expression of the late adenoviral gene L1, L2, L3, L4 and L5. Any vector with at least one promoter replacement is envisioned. For example, combinations of early region replacement include E1A and E1B, E1A and E2, E1B and E2, E1A and E4, E1B and E4, E1A and E5, E1B and E5, E1A and E1B and E2, E1A and E1B and E4, E1A and E1B and E5, E1A and E1B and E2and E4, E1A and E1B and E2 and E5, E1A and E1B and E4 and E5, and E1A and E1B and E2 and E4 and E5.

To further reduce the expression of viral proteins in an adenoviral vector, one or more inducible or synthetic promoters, either of the same or different origin, may be used together to regulate transcription of viral genes. For example, in an E1 region-deleted adenovirus, the GAL4/TATA promoter may be substituted for the adenoviral E4 promoter, as well as the adenoviral E2 promoter, so that expression of the E2 and E4 genes is only possible in producer cells expressing the GAL4/VP16 transactivating polypeptide. Similarly, the GAL4/TATA promoter could be substituted for the E2 promoter, and the GAL4-estrogen receptor response element promoter could be linked to the E4 gene. In such a system (see below), the producer cells would express the GAL4/VP16 fusion polypeptide to drive expression of the E2 gene, as well as the GAL4/ER (estrogen receptor) fusion polypeptide to drive expression of the E4 gene. It is envisioned that any number of synthetic or inducible promoter combinations could be substituted for one or more of the viral gene promoters, thus retaining precise control over the viral gene expression and replication.

Another way the present invention could be utilized is with viral vectors with more than one deleted viral gene. Deletions are meant to include truncations via stop codons. Also contemplated are missense and substitutions mutations of viral genes. Currently, there are adenoviral vectors available that have both the E1 and E3 regions deleted. Because all of the regulatory elements for viral replication and packaging are present in the ends of the adenoviral genome, it is possible to generate adenovirus vectors lacking the function or sequence of all or part of one or more of the E1, E2, E3, E4, E5 L1, L2, L3, L4 and L5 regions, or any combination of these regions. In such a vector, for example, a GAL4/TATA promoter and/or other inducible promoter, is used to drive the remaining viral gene(s). Propagation of this virus then, would require a producer cell to provide in trans the deleted adenovirus gene products, as well as the GAL4/VP16 transactivator to active the inducibly controlled gene. Progeny virus produced by this producer cell line, when transduced into other non-producer cells, would have very low or non-existent expression of the deleted and regulated genes. The resultant cellular toxicity of the vector to the host cell and immunogenicity of the host cell, would be greatly reduced, thereby allowing stable and long term expression of the transgene. Vectors combinations include vectors lacking combinations of E1A and E1B and E2, E1A and E1B and E4, E1A and E1B and E5, E1A and E1B and E2 and E4, E1A and E1B and E2 and E5, and E1A and E1B and E4 and E5. E3 can be deleted from any of the foregoing vectors, but need not be contained in a corresponding cell line as it is non-essential.

Generation of vectors is according to standard methods for manipulation of adenovirus. A preferred embodiment is the use of homologous recombination with cloned adenoviral sequences. Briefly, the entire genome, or at least the majority of the genome is cloned into a plasmid vector allowing for its manipulation. Cotransfection of helper cells (containing viral genes and/or transducing factors for the inducible promoter) with this construct, along with viral sequences that flank the construct to be inserted, will permit recombination of the construct into the viral backbone. Virus can be recovered after isolation by plaque purification, before or after screening for the insert via methods such as Southern analysis or PCR™.

ii) Other Vectors as Expression Constructs

Other viral vectors may be employed as expression constructs in the present invention. Vectors derived from viruses such as vaccinia virus (Ridgeway, 1988; Baichwal and Sugden, 1986; Coupar et al., 1988), adeno-associated virus (AAV) (Ridgeway, 1988; Baichwal and Sugden, 1986; Hermonat and Muzycska, 1984) and herpesviruses may be employed. These viruses offer several features for use in gene transfer into various mammalian cells.

E. Method of Expressing Heterologous Genes

In certain embodiments, the present invention further involves a method for expressing a gene in a mammalian cell. Such methods involve the use of an vector construct containing heterologous DNA encoding the therapeutic gene and a means for its expression, replicating the vector in an appropriate helper cell, obtaining viral particles produced therefrom, and infecting mammalian cells with the recombinant virus particles. The gene could simply encode a protein for which large quantities of the protein are desired, i.e., large scale in vitro production methods. Alternatively, the gene could be at therapeutic gene, for example to treat cancer cells, to express immunomodulatory genes to fight viral infections, or to replace a gene's function as a result of a genetic defect. In the context of the gene therapy vector, gene will be a heterologous DNA, meant to include DNA derived from a source other than the viral genome which provides the backbone of the vector. Finally, the virus may act as a live viral vaccine and express an antigen of interest for the production of antibodies thereagainst. The gene may be derived from a prokaryotic or eukaryotic source such as a bacterium, a virus, a yeast, a plant, or even an animal. The heterologous DNA may also be derived from more than one source, i.e., a multigene construct or a fusion protein. The heterologous DNA may also include a regulatory sequence may be derived from one source and the gene from a different source.

i) Therapeutic Genes p53 currently is recognized as a tumor suppressor gene (Montenarh, 1992). High levels of mutant p53 have been found in many cells transformed by chemical carcinogenesis, ultraviolet radiation, and several viruses, including SV40. The p53 gene is a frequent target of mutational inactivation in a wide variety of human tumors and is already documented to be the most frequently-mutated gene in common human cancers (Mercer, 1992). It is mutated in over 50% of human NSCLC (Hollestein et al., 1991) and in a wide spectrum of other tumors.

The p53 gene encodes a 393-amino-acid phosphoprotein that can form complexes with host proteins such as large-T antigen and E1B. The protein is found in normal tissues and cells, but at concentrations which are generally minute by comparison with transformed cells or tumor tissue. Interestingly, wild-type p53 appears to be important in regulating cell growth and division. Overexpression of wild-type p53 has been shown in some cases to be anti-proliferative in human tumor cell lines. Thus, p53 can act as a negative regulator of cell growth (Weinberg, 1991) and may directly suppress uncontrolled cell growth or directly or indirectly activate genes that suppress this growth. Thus, absence or inactivation of wild-type p53 may contribute to transformation. However, some studies indicate that the presence of mutant p53 may be necessary for full expression of the transforming potential of the gene.

Wild-type p53 is recognized as an important growth regulator in many cell types. Missense mutations are common for the p53 gene and are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991).

Casey and colleagues have reported that transfection of DNA encoding wild-type p53 into two human breast cancer cell lines restores growth suppression control in such cells (Casey et al., 1991). A similar effect has also been demonstrated on transfection of wild-type, but not mutant, p53 into human lung cancer cell lines (Takahasi et al., 1992). p53 appears dominant over the mutant gene and will select against proliferation when transfected into cells with the mutant gene. Normal expression of the transfected p53 is not detrimental to normal cells with endogenous wild-type p53. Thus, such constructs might be taken up by normal cells without adverse effects. It is thus proposed that the treatment of p53-associated cancers with wild-type p53 expression constructs will reduce the number of malignant cells or their growth rate. Furthermore, recent studies suggest that some p53 wild-type tumors are also sensitive to the effects of exogenous p53 expression.

The major transitions of the eukaryotic cell cycle are triggered by cyclin-dependent kinases, or CDK's. One CDK, cyclin-dependent kinase 4 (CDK4), regulates progression through the $G_1$ phase. The activity of this enzyme may be to phosphorylate Rb at late $G_1$. The activity of CDK4 is controlled by an activating subunit, D-type cyclin, and by an inhibitory subunit, e.g., $p16^{INK4}$, which has been biochemically characterized as a protein that specifically binds to and inhibits CDK4, and thus may regulate Rb phosphorylation (Serrano et al., 1993; Serrano et al., 1995). Since the $p16^{INK4}$ protein is a CDK4 inhibitor (Serrano, 1993), deletion of this gene may increase the activity of CDK4, resulting in hyperphosphorylation of the Rb protein. p16 also is known to regulate the function of CDK6.

$p16^{INK4}$ belongs to a newly described class of CDK-inhibitory proteins that also includes $p16^B$, $p21^{WAF1, CIP1, SDI1}$, and $p27^{KIP1}$. The $p16^{INK4}$ gene maps to 9p21, a chromosome region frequently deleted in many tumor types. Homozygous deletions and mutations of the $p16^{INK4}$ gene are frequent in human tumor cell lines. This evidence suggests that the $p61^{INK4}$ gene is a tumor suppressor gene. This interpretation has been challenged, however, by the observation that the frequency of the $p16^{INK4}$ gene alterations is much lower in primary uncultured tumors than in cultured cell lines (Caldas et al., 1994; Cheng et al., 1994; Hussussian et al., 1994; Kamb et al., 1994a; Kamb et al., 1994b; Mori et al., 1994; Okamoto et al., 1994; Nobori et al., 1995; Orlow et al., 1994; Arap et al., 1995). Restoration of wild-type $p16^{INK4}$ function by transfection with a plasmid expression vector reduced colony formation by some human cancer cell lines (Okamoto, 1994; Arap, 1995).

C-CAM is expressed in virtually all epithelial cells (Odin and Obrink, 1987). C-CAM, with an apparent molecular weight of 105 kD, was originally isolated from the plasma membrane of the rat hepatocyte by its reaction with specific antibodies that neutralize cell aggregation (Obrink, 1991). Recent studies indicate that, structurally, C-CAM belongs to the immunoglobulin (Ig) superfamily and its sequence is highly homologous to carcinoembryonic antigen (CEA) (Lin and Guidotti, 1989). Using a baculovirus expression system, Cheung et al. (1993a; 1993b and 1993c) demonstrated that the first Ig domain of C-CAM is critical for cell adhesion activity.

Cell adhesion molecules, or CAMs are known to be involved in a complex network of molecular interactions that regulate organ development and cell differentiation (Edelman, 1985). Recent data indicate that aberrant expression of CAMs maybe involved in the tumorigenesis of several neoplasms; for example, decreased expression of E-cadherin, which is predominantly expressed in epithelial cells, is associated with the progression of several kinds of neoplasms (Edelman and Crossin, 1991; Frixen et al., 1991; Bussemakers et al., 1992; Matsura et al., 1992; Umbas et al., 1992). Also, Giancotti and Ruoslahti (1990) demonstrated that increasing expression of $\alpha_5\beta_1$ integrin by gene transfer can reduce tumorigenicity of Chinese hamster ovary cells in vivo. C-CAM now has been shown to suppress tumors growth in vitro and in vivo.

Other tumor suppressors that may be employed according to the present invention include RB, APC, DCC, NF-1, NF-2, WT-1, MEN-I, MEN-II, zac1, p73, BRCA1, VHL, FCC, MMAC1, MCC, p16, p21, p57, C-CAM, p27 and BRCA2. Inducers of apoptosis, such as Bax, Bak, Bcl-$X_s$, Bik, Bid, Harakiri, Ad E1B, Bad and ICE-CED3 proteases, similarly could find use according to the present invention.

Various enzyme genes are of interest according to the present invention. Such enzymes include cytosine deaminase, hypoxanthine-guanine phosphoribosyltransferase, galactose-1-phosphate uridyltransferase, phenylalanine hydroxylase, glucocerbrosidase, sphingomyelinase, α-L-iduronidase, glucose-6-phosphate dehydrogenase, HSV thymidine kinase and human thymidine kinase.

Hormones are another group of gene that may be used in the vectors described herein. Included are growth hormone, prolactin, placental lactogen, luteinizing hormone, follicle-stimulating hormone, chorionic gonadotropin, thyroid-stimulating hormone, leptin, adrenocorticotropin (ACTH), angiotensin I and II, β-endorphin, β-melanocyte stimulating hormone (β-MSH), cholecystokinin, endothelin I, galanin, gastric inhibitory peptide (GIP), glucagon, insulin, lipotropins, neurophysins, somatostatin, calcitonin, calcitonin gene related peptide (CGRP), β-calcitonin gene related peptide, hypercalcemia of malignancy factor (1–40), parathyroid hormone-related protein (107–139) (PTH-rP), parathyroid hormone-related protein (107–111) (PTH-rP), glucagon-like peptide (GLP-1), pancreastatin, pancreatic peptide, peptide YY, PHM, secretin, vasoactive intestinal peptide (VIP), oxytocin, vasopressin (AVP), vasotocin, enkephalinamide, metorphinamide, α melanocyte stimulating hormone (α-MSH), atrial natriuretic factor (5–28) (ANF), amylin, amyloid P component (SAP-1), corticotropin releasing hormone (CRH), growth hormone releasing factor (GHRH), luteinizing hormone-releasing hormone (LHRH), neuropeptide Y, substance K (neurokinin A), substance P and thyrotropin releasing hormone (TRH).

Other classes of genes that are contemplated to be inserted into the vectors of the present invention include interleukins and cytokines. Interleukin 1 (IL-1), IL-2, IL-3, IL-4, IL-5, IL-6, IL-7, IL-8, IL-9, IL-10, IL-11 IL-12, GM-CSF and G-CSF.

Examples of other diseases for which the present adenoviral vector would be useful for include but are not limited to adenosine deaminase deficiency, human blood clotting factor IX deficiency in hemophilia B, and cystic fibrosis, which would involve the replacement of the cystic fibrosis transmembrane receptor gene. The vectors embodied in the present invention could also be used for treatment of hyperproliferative disorders such as rheumatoid arthritis or restenosis by transfer of genes encoding angiogenesis inhibitors or cell cycle inhibitors. Transfer of prodrug activators such as the HSV-TK gene can be also be used in the treatment of hyperploiferative disorders, including cancer.

ii) Antisense Constructs

Oncogenes such as ras, myc, neu, raf, erb, src, fms, jun, trk; ret, gsp, hst, bcl and abl also are suitable targets. However, for therapeutic benefit, these oncogenes would be expressed as an antisense nucleic acid, so as to inhibit the expression of the oncogene. The term "antisense nucleic acid" is intended to refer to the oligonucleotides complementary to the base sequences of oncogene-encoding DNA and RNA. Antisense oligonucleotides, when introduced into a target cell, specifically bind to their target nucleic acid and interfere with transcription, RNA processing, transport and/or translation. Targeting double-stranded (ds) DNA with oligonucleotide leads to triple-helix formation; targeting RNA will lead to double-helix formation.

Antisense constructs may be designed to bind to the promoter and other control regions, exons, introns or even exon-intron boundaries of a gene. Antisense RNA constructs, or DNA encoding such antisense RNAs, may be employed to inhibit gene transcription or translation or both within a host cell, either in vitro or in vivo, such as within a host animal, including a human subject. Nucleic acid sequences which comprising "complementary nucleotides" are those which are capable of base-pairing according to the standard Watson-Crick complementary rules. That is, that the larger purines will base pair with the smaller pyrimidines to form only combinations of guanine paired with cytosine (G:C) and adenine paired with either thymine (A:T), in the case of DNA, or adenine paired with uracil (A:U) in the case of RNA.

As used herein, the terms "complementary" or "antisense sequences" mean nucleic acid sequences that are substantially complementary over their entire length and have very few base mismatches. For example, nucleic acid sequences of fifteen bases in length may be termed complementary when they have a complementary nucleotide at thirteen or fourteen positions with only a single mismatch. Naturally, nucleic acid sequences which are "completely complementary" will be nucleic acid sequences which are entirely complementary throughout their entire length and have no base mismatches.

While all or part of the gene sequence may be employed in the context of antisense construction, statistically, any sequence of 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that oligonucleotides of 8, 9, 10, 11, 12, 13, 14, 15, 16, 17, 18, 19, 20 or more base pairs will be used. One can readily determine whether a given antisense nucleic acid is effective at targeting of the corresponding host cell gene simply by testing the constructs in vitro to determine whether the endogenous gene's function is affected or whether the expression of related genes having complementary sequences is affected.

In certain embodiments, one may wish to employ antisense constructs which include other elements, for example, those which include C-5 propyne pyrimidines. Oligonucleotides which contain C-5 propyne analogues of uridine and cytidine have been shown to bind RNA with high affinity and to be potent antisense inhibitors of gene expression (Wagner et al., 1993).

As an alternative to targeted antisense delivery, targeted ribozymes may be used. The term "ribozyme" is refers to the an RNA-based enzyme capable targeting cleaving particular base sequences in oncogene DNA and RNA. Ribozymes can either be targeted directly to cells, in the form of RNA oligo-nucleotides incorporating ribozyme sequences, or introduced into the cell as an expression construct encoding the desired ribozymal RNA. Ribozymes may be used and applied in much the same way as described for antisense nucleic acids.

iii) Antigens for Vaccines

Other therapeutics genes might include genes encoding viral antigens such as viral antigens, bacterial antigens, fungal antigens or parasitic antigens. Viruses include picornavirus, coronavirus, togavirus, flavirviru, rhabdovirus, paramyxovirus, orthomyxovirus, bunyavirus, arenvirus, reovirus, retrovirus, papovavirus, parvovirus, herpesvirus, poxvirus, hepadnavirus, and spongiform virus. Preferred viral targets include influenza, herpes simplex virus 1 and 2, measles, small pox, polio or HIV. Pathogens include trypanosomes, tapeworms, roundworms, helminths. Also, tumor markers, such as fetal antigen or prostate specific antigen, may be targeted in this manner. Preferred examples include HIV env proteins, hepatitis B surface antigen. Administration of a vector according to the present invention for vaccination purposes would require that the vector-associated antigens be sufficiently non-immunogenic to enable long term expression of the transgene, for which a strong immune response would be desired. Preferably, vaccination of an individual would only be required infrequently, such as yearly or biennially, and provide long term immunologic protection against the infectious agent.

iv) Single-Chain Antibodies

In yet another embodiment, the heterologous gene may include a single-chain antibody. Methods for the production of single-chain antibodies are well known to those of skill in the art. The skilled artisan is referred to U.S. Pat. No. 5,359,046, (incorporated herein by reference) for such methods. A single chain antibody is created by fusing together the variable domains of the heavy and light chains using a short peptide linker, thereby reconstituting an antigen binding site on a single molecule.

Single-chain antibody variable fragments (Fvs) in which the C-terminus of one variable domain is tethered to the N-terminus of the other via a 15 to 25 amino acid peptide or linker, have been developed without significantly disrupting antigen binding or specificity of the binding (Bedzyk et al., 1990; Chaudhary et al., 1990). These Fvs lack the constant regions (Fc) present in the heavy and light chains of the native antibody.

v) Control Regions

In order for the viral vector to effect expression of a transcript encoding a therapeutic gene, the polynucleotide encoding the therapeutic gene will be under the transcriptional control of a promoter and a polyadenylation signal. A "promoter" refers to a DNA sequence recognized by the synthetic machinery of the host cell, or introduced synthetic machinery, that is required to initiate the specific transcription of a gene. A polyadenylation signal refers to a DNA sequence recognized by the synthetic machinery of the host cell, or introduced synthetic machinery, that is required to direct the addition of a series of nucleotides on the end of the mRNA transcript for proper processing and trafficking of the transcript out of the nucleus into the cytoplasm for translation. The phrase "under transcriptional control" means that the promoter is in the correct location in relation to the polynucleotide to control RNA polymerase initiation and expression of the polynucleotide.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription.

The particular promoter that is employed to control the expression of a therapeutic gene is not believed to be critical, so long as it is capable of expressing the polynucleotide in the targeted cell. Thus, where a human cell is targeted, it is preferable to position the polynucleotide coding region adjacent to and under the control of a promoter that is capable of being expressed in a human cell. Generally speaking, such a promoter might include either a human or viral promoter. A list of promoters is provided in the following table:

TABLE 1

| PROMOTER |
| --- |
| Immunoglobulin Heavy Chain |
| Immunoglobulin Light Chain |
| T-Cell Receptor |
| HLA DQ α and DQ β |
| β-Interferon |
| Interleukin-2 |
| Interleukin-2 Receptor |
| MHC Class II 5 |
| MHC Class II HLA-DRα |
| β-Actin |
| Muscle Creatine Kinase |
| Prealbumin (Transthyretin) |
| Elastase I |
| Metallothionein |
| Collagenase |
| Albumin Gene |
| α-Fetoprotein |
| τ-Globin |
| β-Globin |
| c-fos |
| c-HA-ras |
| Insulin |
| Neural Cell Adhesion Molecule (NCAM) |
| $\alpha_{1\text{-Antitrypsin}}$ |
| H2B (TH2B) Histone |
| Mouse or Type I Collagen |
| Glucose-Regulated Proteins (GRP94 and GRP78) |
| Rat Growth Hormone |
| Human Serum Amyloid A (SAA) |
| Troponin I (TN I) |
| Platelet-Derived Growth Factor |
| Duchenne Muscular Dystrophy |
| SV40 |
| Polyoma |
| Retroviruses |
| Papilloma Virus |
| Hepatitis B Virus |
| Human Immunodeficiency Virus |
| Cytomegalovirus |
| Gibbon Ape Leukemia Virus |

The promoter further may be characterized as an inducible promoter. An inducible promoter is a promoter which is inactive or exhibits low activity except in the presence of an inducer substance. Some examples of promoters that may be included as a part of the present invention include, but are not limited to, MT II, MMTV, Colleganse, Stromelysin, SV40, Murine MX gene, α-2-Macroglobulin, MHC class I gene h-2 kb, HSP70, Proliferin, Tumor Necrosis Factor, or Thyroid Stimulating Hormone α gene. It is understood that any inducible promoter may be used in the practice of the present invention and that all such promoters would fall within the spirit and scope of the claimed invention.

TABLE 2

| Element | Inducer |
| --- | --- |
| MT II | Phorbol Ester (TPA) |
|  | Heavy metals |
| MMTV (mouse mammary tumor virus) | Glucocorticoids |
| β-Interferon | poly(rI)X |
|  | poly(rc) |
| Adenovirus 5 E2 | E1a |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2 kb | Interferon |
| HSP70 | E1a, SV40 Large T Antigen |
| Proliferin | Phorbol Ester-TPA |
| Tumor Necrosis Factor | FMA |
| Thyroid Stimulating Hormone α Gene | Thyroid Hormone |

In various embodiments, the human cytomegalovirus (CMV) immediate early gene promoter, the SV40 early promoter and the Rous sarcoma virus long terminal repeat can be used to obtain high-level expression of the polynucleotide of interest. The use of other viral or mammalian cellular or bacterial phage promoters which are well-known in the art to achieve expression of polynucleotides is contemplated as well, provided that the levels of expression are sufficient to produce a growth inhibitory effect.

By employing a promoter with well-known properties, the level and pattern of expression of a polynucleotide following transfection can be optimized. For example, selection of a promoter which is active in specific cells, such as tyrosinase (melanoma), α-fetoprotein and albumin (liver tumors), CC10 (lung tumor) and prostate-specific antigen (prostate tumor) will permit tissue-specific expression of the therapeutic gene.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Additionally any promoter/enhancer combination (as per the Eukaryotic Promoter Data Base (EPDB)) could also be used to drive expression of a particular construct. Use of a T3, T7 or SP6 cytoplasmic expression system is another possible embodiment. Eukaryotic cells can support cytoplasmic transcription from certain bacteriophage promoters if the appropriate bacteriophage polymerase is provided, either as part of the delivery complex or as an additional genetic expression vector.

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed. Such polyadenylation signals such as that from SV40, bovine growth hormone, and the herpes simplex virus thymidine kinase gene have been found to function well in a number of target cells.

vi) In vitro Protein Production

Following transduction with a viral vector according to the present invention, primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented and are disclosed herein by reference (Freshner, 1992).

One embodiment of the foregoing involves the use of gene transfer to immortalize cells for the production of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question.

Examples of useful mammalian host cell lines are Vero and HeLa cells and cell lines of Chinese hamster ovary, W138, BHK, COS-7, 293, HepG2, 3T3, RIN and MDCK cells. In addition, a host cell strain may be chosen that modulates the expression of the inserted sequences, or modifies and process the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, HSV thymidine kinase, hypoxanthine-guanine phosphoribosyltransferase and adenine phosphoribosyltransferase genes, in tk-, hgprt- or aprt- cells, respectively. Also, anti-metabolite resistance can be used as the basis of selection for dhfr, that confers resistance to; gpt, that confers resistance to mycophenolic acid; neo, that confers resistance to the aminoglycoside G418; and hygro, that confers resistance to hygromycin.

Animal cells can be propagated in vitro in two modes: as non-anchorage dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent cells.

Large scale suspension culture of mammalian cells in stirred tanks is a common method for production of recombinant proteins. Two suspension culture reactor designs are in wide use—the stirred reactor and the airlift reactor. The stirred design has successfully been used on an 8000 liter capacity for the production of interferon (Phillips et al., 1985; Mizrahi, 1983). Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easily, has good mass transfer of gases and generates relatively low shear forces.

In certain embodiments of the invention, it will be desirable to produce functional polypeptide or variants thereof. Protein purification techniques are well known to those of skill in the art. These techniques tend to involve the fractionation of the cellular milieu to separate the polypeptides from other components of the mixture. Having separated polypeptides from the other components, the polypeptide sample may be purified using chromatographic and electrophoretic techniques to achieve complete purification. Analytical methods particularly suited to the preparation of a pure peptide are ion-exchange chromatography, exclusion chromatography; polyacrylamide gel electrophoresis; isolectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number". The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater -fold purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of min, or at most an h. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

F. Methods of Gene Transfer

In order to create the helper cell lines of the present invention, and to create recombinant adenovirus vectors for use therewith, various genetic (i.e., DNA) constructs must be delivered to a cell. One way to achieve this is via viral transductions, for example, by transformation with retrovirus or bovine papilloma virus, both of which permit permanent transformation of a host cell with a gene(s) of interest.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979), cell sonication (Fechheimer et al., 1987), gene bombardment using high velocity microprojectiles (Yang et al., 1990), and receptor-mediated transfection (Wu and Wu, 1987; Wu and Wu, 1988).

Once the construct has been delivered into the cell the nucleic acid encoding the therapeutic gene may be positioned and expressed at different sites. In certain embodiments, the nucleic acid encoding the therapeutic gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In one embodiment of the invention, the expression construct may simply consist of naked recombinant DNA or plasmids. Transfer of the construct may be performed by any of the methods mentioned above which physically or chemically permeabilize the cell membrane. This is particularity applicable for transfer in vitro, however, it may be applied for in vivo use as well. Dubensky et al. (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. It is envisioned that DNA encoding a CAM may also be transferred in a similar manner in vivo and express CAM.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991).

Liposome-mediated nucleic acid delivery and expression of foreign DNA in vitro has been very successful. Using the β-lactamase gene, Wong et al. (1980) demonstrated the feasibility of liposome-mediated delivery and expression of foreign DNA in cultured chick embryo, HeLa, and hepatoma cells. Nicolau et al. (1987) accomplished successful liposome-mediated gene transfer in rats after intravenous injection. Also included are various commercial approaches involving "lipofection" technology.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear nonhistone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention.

Other expression constructs which can be employed to deliver a nucleic acid encoding a therapeutic gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al, 1993; Perales et al, 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a nucleic acid encoding a therapeutic gene also may be specifically delivered into a cell type such as prostate, epithelial or tumor cells, by any number of receptor-ligand systems with or without liposomes. For example, the human prostate-specific antigen (Watt et al, 1986) may be used as the receptor for mediated delivery of a nucleic acid in prostate tissue.

G. Pharmaceutical Compositions and Routes of Administration

Where administration of a viral vector according to the present invention is contemplated, it will be necessary to prepare the complex as a pharmaceutical composition appropriate for the intended application. Generally this will entail preparing a pharmaceutical composition that is essentially free of pyrogens, as well as any other impurities that could be harmful to humans or animals. One also will generally desire to employ appropriate salts and buffers to render the complex stable and allow for complex uptake by target cells.

Aqueous compositions of the present invention comprise an effective amount of the expression construct and nucleic acid, dissolved or dispersed in a pharmaceutically acceptable carrier or aqueous medium. Such compositions can also be referred to as inocula. The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

Solutions of the active compounds as free base or pharmacologically acceptable salts can be prepared in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The viral constructs of the present invention may include classic pharmaceutical preparations. Administration of therapeutic compositions according to the present invention will be via any common route so long as the target tissue is available via that route. This includes oral, nasal, buccal, rectal, vaginal or topical. Alternatively, administration will be by orthotopic, intradermal subcutaneous, intramuscular, intraperitoneal, or intravenous injection. Such compositions would normally be administered as pharmaceutically acceptable compositions that include physiologically acceptable carriers, buffers or other excipients. For application against tumors, direct intratumoral injection, inject of a resected tumor bed, regional (i.e., lymphatic) or general administration is contemplated. It also may be desired to perform continuous perfusion over h or d via a catheter to the tumor or tumor site.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain about 100 mg of human serum albumin per milliliter of phosphate buffered saline. Other pharmaceutically acceptable carriers include aqueous solutions, non-toxic excipients, including salts, preservatives, buffers and the like may be used. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

Additional formulations which are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

An effective amount of the therapeutic agent is determined based on the intended goal, for example (i) inhibition of tumor cell proliferation, (ii) elimination or killing of tumor cells, (iii) vaccination, or (iv) gene transfer for long term expression of a therapeutic gene. The term "unit dose" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the subject to be treated, the state of the subject and the result desired. Multiple gene therapeutic regimens are expected, especially for adenovirus.

In certain embodiments of the present invention, an adenoviral vector encoding a tumor suppressor gene will be used to treat cancer patients. Typical amounts of an adenovirus vector used in gene therapy of cancer is $10^3$–$10^{15}$ PFU/dose, ($10^3$, $10^4$, $10^5$, $10^6$, $10^7$, $10^8$, $10^9$, $10^{10}$, $10^{11}$, $10^{12}$, $10^{13}$, $10^{14}$, $10^{15}$) wherein the dose be divided into several injections at different sites within a solid tumor. The treatment regimen also involves several cycles of administration of the gene transfer vector over a period of 3–10 wk. Administration of the vector for longer periods of time from months to years may be necessary for continual therapeutic benefit.

In another embodiment of the present invention, an adenoviral vector encoding a therapeutic gene may be used to vaccinate humans or other mammals. Typically, an amount of virus effective to produce the desired effect, in this case vaccination, would be administered to a human or mammal so that long term expression of the transgene is achieved and a strong host immune response develops. It is contemplated that a series of injections, for example, a primary injection followed by two booster injections, would be sufficient to induce an long term immune response. A typical dose would be from $10^6$ to $10^{15}$ PFU/injection depending on the desired result. Low doses of antigen generally induce a strong cell-mediated response, whereas high doses of antigen generally induce an antibody-mediated immune response. Precise amounts of the therapeutic composition also depend on the judgment of the practitioner and are peculiar to each individual.

EXAMPLES

The following examples are included to demonstrate preferred embodiments of the invention. It should be appreciated by those of skill in the art that the techniques disclosed in the examples which follow represent techniques discovered to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Methods and Materials

Cell culture. H1299 cells (obtained from Drs. Adi Gazdar and John Minna, University of Texas Southwestern, Dallas, Tex.) and A549 (American Type Culture Collection, Rockville, Md.) were derived from human non-small cell lung cancers. All cell lines were cultured at 37° C. in a humidified atmosphere of 95% air and 5% $CO_2$. 293 cells and A549 cells were maintained in Dulbecco's modified Eagle's medium (DMEM) containing 4.5 g/l glucose with 10% FBS. Syngenetic 1422 cell line derived from C3H/HeN tumor was obtained from Dr. Amanthaswarmy at MDACC, Houston, Tex. and CL4/SV40 cell line derived from C57BL/6 mouse fibroblast transformed by SV40 was obtained from ATCC, and both cell lines were maintained in DMEM with 10% FBS. H1299 cells were cultured in RPMI 1640 supplemented with 5% FBS. Penicillin (100 U/ml) and streptomycin (1000 mg/ml) were included in the culture media. For selection of neomycin-resistant cells, G418 (400 mg/ml) was included in the medium.

In certain other studies, the 293 cell line and the 293/GV16 cell line expressing yeast GAL4/VP16 transactivating proteins (Fang et al., 1997) were used for adenovirus construction, amplification and titration.

Construction of recombinant adenovirus vectors. The Ad/RSV-hFIX vector was constructed as previously described (Fang et al., 1996). A 1.4-kb hFIX cDNA was inserted into the HindIII site of pAdL.2/RSV. The resulting transfer plasmid, pAdL.2/RSV-hFIX, and pJM17 (obtained from Dr. Frank Graham, McMaster University) were then cotransduced into 293 cells by calcium phosphate (Graham and Van Der Eb, 1973). Recombinant virus from a single plaque was identified by ELISA, which detected the presence of hFIX in the medium of cells transduced with the virus. AdE4A/RSV-hFIX and AdE4B/RSV-hFIX were constructed by cotransfecting of 293/GV16 cells with a 27-kb SrfI fragment from Ad/RSV-hFIX and either transfer plasmid pBF7A (for AdE4A/RSV-hFIX) or pBF7B (for AdE4B/RSV-LTR). pBF7A and pBF7B were constructed on a pNEB193 backbone (New England Biolabs, Beverly, Mass.); both contained adenoviral sequences between map units 70 and 100 and differed only in the right end of their terminal repeats. The deletion in the E4 promoter region in pBF7A reached from nucleotide 35575 to 35786 of the adenovirus type 5 (Ad5) genome; that in pBF7B reached from 35575 to 35818. In both plasmids, a synthetic promoter containing a minimal TATA box and five consensus 17-mer yeast GAL4-binding-site elements (Sadowski et al., 1992) was introduced into the region left vacant by the E4 promoter deletion. The detailed cloning procedure will be provided upon request. The recombinant AdE4A/RSV-hFIX and AdE4B/RSV-hFIX were then identified by PCR™ with a pair of primers amplifying adenoviral sequences from 35460 to 35935. Virus from a single plaque was expanded in 293 cells (Ad/RSV-hFIX) or 293/GV16 cells (AdE4A/RSV-hFIX and AdE4B/RSV-hFIX) and twice purified through ultracentrifugation on a cesium chloride gradient. Virus titers were determined by both optical absorbance (one $A_{260}$ unit=$10^{12}$ particles/ml) and plaque assay (Graham and Prevec, 1991).

In certain of the studies, viruses were produced in GAL4-VP16 transformed 293 cells (GV16/293). E1 and E3 were deleted in the backbone of all adenovirus vectors. Transgenes were inserted into the E1 deleted region. Viruses were propagated in either 293 cells or VP16/293 cells (Fang et al., 1997) and purified with two times of CsCl gradient centrifugation. Viral titers were determined by both O.D measurement and plaque assay. DNA structures of the p53 gene and GAL4/TATA sequences were confirmed by automatic DNA sequencing. Potential contamination of the wild type virus in the viral preparation were accessed by PCR™ analysis.

The Ad/RSV-Luc vector was constructed similarly to the methods outlined above for Ad/RSV-hFIX (Zhang et al., 1994). Vectors Ad/GT-Luc, Ad/GT-LacZ (adenoviral vector containing reporter β-galactosidase cDNA driven by GAL4/TATA), Ad/PO-Luc, and Ad/PGK-GV16 (FIG. 6) were constructed as described previously (Fang et al., 1994). Luciferase cDNA was cut out from pGL3-Basic Vector (Promega, Madison, Wis.). The GAL4/TATA promoter (GT) consisting of five consensus 17-mer GAL4 sites upstream from the adenovirus E1B TATA box was derived from pG5EC (obtained from Dr. I. Sadowski University of British Columbia, Vancouver, Canada). To construct Ad/PGK-GV16, cDNA for the GAL4/VP16 fusion protein was excised from plasmid pM2/VP16 (obtained from Dr. Sadowski) and placed downstream of the mouse 3-phosphoglycerate kinase (PGK) gene promoter (McBurney et al., 1992). Recombinant virus from a single plaque was identified by DNA analysis, then expanded in 293 cells and twice purified by ultracentrifugation on a cesium chloride gradient. Virus titers were determined by both optical absorbance at $A_{260}$ (one $A_{260}$ unit=$10^{12}$ particles/ml) and by median tissue culture infective dose ($TCID_{50}$) assays as described previously (Huyghe et al., 1995). Titers determined by $TCID_{50}$ assay were used in subsequent studies.

Biochemical analysis. Transfection of plasmid DNA into cultured cells was carried out by calcium phosphate method (Graham and Van Der Eb, 1973). Cells were harvested at 48 h posttransfection and resuspended in 50 mM TrisCl pH 7.4, and 2 mM dithiothreitol. The cell suspension was frozen and thawed three times, and the cell debris was removed by microcentrifugation. Protein concentration was performed with a kit from Pierce (Rockford, Ill.) following the manufacturer's instructions. The CAT assay was performed as described (Sambrook et al., 1989). β-galactosidase activities were measured with 0-nitrophenyl-β-D-galactopyranoside as previously described (Neumann et al., 1987). The ELISA for quantitation of hFIX antigen was performed using a polyclonal rabbit anti-hFIX antibody (Dako, Carpinteria, Calif.) as both the primary and secondary antibody. Conjugation of horse radish peroxidase (Pierce, Rockford, Ill.) to the anti-hFIX antibody and ELISA were performed as previously described (Hornbeck, 1994). All assays were performed in duplicate.

In other examples, cultured cells were lysed or tissues from Balb/c mice were homogenized in luciferase assay buffer. Cell or tissue debris was then removed by microcentrifugation. Protein concentrations were determined using a kit from BRL (Gaithersburg, Md.) according to the manufacturer's instructions. Luciferase activities were determined using a luminometer and a luciferase assay system according to the manufacturer's instructions (Promega, Madison, Wis.).

Immunostaining. Fluorescein (FITC)-labeled anti-Ad5 antibody (Chemicon International, Temecula, Calif.) was used for detection of hexon expression and for $TCID_{50}$ assays. To detect hexon expression in cultured cells transduced with recombinant adenovirus, cells plated in 96-well microtiter plates were infected with virus at the indicated MOI in duplicate and cultured for 2 d. The cells were then fixed with 50% acetone-50% methanol and washed with PBS. FITC-labeled anti-hexon antibody was added to the fixed cells and incubated for 45 min at 37° C. After washing with PBS, the plate was examined under a fluorescent microscope for the presence of label. Mock infection was used as negative control.

Histopathologic Analysis. Formoline-fixed and parafin-embedded liver sections were stained with hematoxylin and eosin. Five infected sections of each of three animals were examined and quantified for pathological changes. Virus induced hepatic animals intimation, necrosis, degeneration, bile duct proliferation were double blindly scored based on the severity of pathological features: 0 characterized as non-infected tissue or no significant lesions observed; 1 as mild; 2 as moderate; 3 as marked; and 4 as severe. Apoptosis was detected by in situ immunohistochemistry stain of frozen liver tissue sections using TUNEL reaction with FITC-labeled dUTP and the degree of apoptosis was scored accordingly.

Immunohistochemistry. Liver tissues were frozen with OTC and cryosectioned (4 micron thick). Sections were fixed in cold acetone for 10 min and rinsed in three changes of PBS. Samples were incubated in PBS with 10% normal serum for 20 min at room temperature and washed once with PBS. For adenoviral hexon staining, samples were incubated with FITC-conjugated mouse anti-hexon monoclonal antibody (0.1–2.0 µg/ml in PBS-BSA) (Chemicon International Inc. Temecula, Calif.) or FITC-conjugated mouse anti-human p53 monoclonal antibody (0.1–2.0 µg/ml in PBS-BSA) for 30 min at 37° C. in the dark. Apoptosis was detected by in situ immunohistochemistry stain of frozen liver tissue sections using TUNEL reaction with FITC-labeled dUTP (Boehringer Mannheim Biochemicals, Indianapolis, Ind.). Sections were washed twice with PBS and mounted with Fluorescence mounting medium (Vector Laboratories, Inc., Burlingame, Calif.). Specimens were examined under a fluorescence microscope.

$TCID_{50}$ assay. $TCID_{50}$ (Tissue Culture Infectious Dose) assays were accomplished in 293/GV16 cells as previously described (Huyghe et al., 1995). The titer was determined using the Titerprint Analysis program (Huyghe et al., 1995).

Northern analysis. Total RNA was isolated with Trizol-Reagent (GIBCO-BRL, Gaithersburg, Mass.) from cultured cells 48 h after infection with recombinant adenovirus. RNA was denatured and fractionated by electrophoresis through a 1.2% agarose gel (20 µg/lane) and blotted onto a nylon membrane. DNA probes specific for adenoviral E4, fiber, and human actin genes were purified from agarose gel after restriction and fractionation by electrophoresis of the plasmids containing those sequences. DNA probes were labeled with ($^{32}P$)dCTP by random oligonucleotide priming (Boehringer Mannheim, Indianapolis, Ind.). Prehybridization and hybridization were carried out in QuikHyb hybridization solution (Stratagene, La Jolla, Calif.) following the manufacturer's instructions. The blots were washed twice in 2×SSC, 0.1% SDS at room temperature for 15 min and once in 0.2×SSC, 0.1% at 60° C. for 25 min.

Southern Blot Analysis. Adenovirus replication in H1299 cells was analyzed by Southern blot. Cells ($5\times10^7$ cells) were seeded in a 100 mm dish and infected with adenoviruses at MOI of 10 and 80 (pfu/cell). Cells were harvested on 1, 3, and 7 d after viral inoculation. Cellular DNA was isolated using Trizol reagent (Life Technology, Houston, Tex.). 20 µg of DNA was digested with BamHI and fragmentated on a 0.8% agarose gel. DNA fragments were transferred to a nylon membrane (GeneScreen, NEW Research Products, Boston, Mass.) and viral DNA was probed with a $^{32}P$-labeled E4orf6 DNA fragment (910 bp). Images were generated and analyzed using a Phosphoimage Analysis System (Molecular Dynamics, Sunnyvale, Calif.).

Western Blot Analysis. Cells grown in 100 mm dishes ($2$–$5\times10^7$/dish) were treated with adenoviruses using PBS as control. Cells were harvested, rinsed once with PBS, and lysed with SDS-PAGE loading buffer. Total proteins were assayed by the BCA method (Pierce, Rockford, Ill.). Each lane was loaded with 20 µg of cell lysate protein and electrophoresed at 100 V for 1–2h. Proteins were transferred from the gel to a Hybond-ECL membrane (Amersham International, England). Membranes were blocked in blocking solution (3% dry milk, 0.1% Tween 20 in PBS) for 1 h at room temperature. Membranes were incubated with 1:500 to 1:1000 dilution of mouse anti-human p53 (Santa Cruz Biotechnology, Inc., Santa Cruz, Calif.) and anti-adenovirus hexon (Chemicon International Inc., Temecula, Calif.) monoclonal antibodies. Immunocomplex was detected using a ECL kit (Amersham) according to the manufacturer's instruction.

DNA assay. Viral DNA was isolated from purified viral preparations. Any E1 wild-type adenoviral contamination was detected with PCR™ as described (Fang et al., 1996). Analysis of the viral E4 region was performed using the same PCR™ procedure as that for E1 region, except that the primers used were 5'-CCTAGGCAAAATAGC-3' (SEQ ID NO:1), and 5'CATCATCAATAATATAC-3' (SEQ ID NO:2), located at map units 98.7 and 100 of the adenoviral genome, respectively. The PCR™ products from the E4 wild-type, AdE4A/RSV-hFIX, and AdE4B/RSV-hFIX vectors were 473 bp, 414 bp, and 381 bp, respectively. Since a SphI site was introduced into AdE4A/RSV-hFIX and AdE4B/RSV-hFIX between the right end of the viral genome and GAL4/TATA during the cloning procedure, the PCR™ products from these two constructs could be digested into two fragments with SphI. Digestion of the PCR™ products with SphI was performed by adding 5 µl of SphI to 10 µl of the final PCR™ mixture and incubating at 37° C. for 1 h. All PCR™ analyses were performed with either a known viral DNA or plasmid DNA as positive control and buffer alone as negative control.

Cellular DNA from cells transfected with recombinant adenoviruses was isolated as previously described (Sambrook et al., 1989). The DNA (5 µg/sample) was digested with Cla and fractionated on 1% agarose gel. Southern blot analysis was performed as described (Sambrook et al., 1989). The plasmid pADL.2/RSV (Fang et al., 1994) was used as a probe to detect the viral genome. Prehybridization and hybridization were performed in QuikHyb hybridization solution (Stratagene, La Jolla, Calif.) following the manufacturer's instructions.

DNA was also isolated from tissues of Balb/c mice infused with vectors or buffer alone. A semiquantitative assay of viral DNA in the tissues was performed via the polymerase chain reaction (PCR™) as described previously (Fang et al., 1994). The following PCR™ primers were used: 5'-TGCCTAGGCAAAATAG-3' (SEQ ID NO:3) and 5'-CATCATCAATAATATAC-3' (SEQ ID NO:4), located at the right end of the adenovirus genome.

Determination of Cell Growth Rate. Inhibition of cell growth by adenovirus infection was assayed by MTT staining (Sigma, St. Louis, Mo.). Experimentally treated cells were harvested and 200 µl of cell suspension were added to each well in a 96 well plates. One tenth volume of MTT solution (5 mg MTT/ml PBS) was added to each well and plate was incubated for 2 to 4 h at 37° C. until the purple precipitate were visible. The medium was carefully removed and precipitates were dissolved in 100 µl of DMSO. The number of viable cells was determined by measuring absorbency at 570 nm with background subtraction at 630–690 nm and calculated by comparing with known numbers of cells. Growth rate was plotted as the percentage of control group.

Apoptosis Analysis. Apoptosis was analyzed by flow cytometry using TUNEL (terminal deoxynucleotidyl transferase-mediated dUTP nick end labeling) reaction with fluorescein isothiocyanate (FITC)-labeled dUTP (Boehringer Mannheim Biochemicals, Germany). Cells were seeded in 60 mm plates and infected with adenovirus constructs using PBS as control. Cells were harvested by centrifugation at 300×g for 10 min and washed twice with PBS. Cells (1–2×10$^7$) were fixed in 1% formaldehyde for 15 min at 4° C. and permeablized in 100 µl of 0.1% Triton X-100, 0.1% sodium titrate solution for 2 min on ice. Cells were washed twice with PBS, resuspended in 50 µl of TUNEL reaction mixture (0.2 M potassium cacodylate, 25 mM Tris-HCl, pH 6.6, 2.5 mM Cobalt Chloride, 0.25 mg/ml BSA, 100 U/ml TdT, 10 µM FITC-dUTP), and incubated for 60 min at 37° C. in a humidified atmosphere in the dark. After incubation, cells were washed twice in PBS and resuspended in 250 to 500 µl of PBS. Apoptosis were analyzed for DNA fragmentation by flow cytometry.

CTL assay. Two to three wk after immunization by I.V. injection of adenoviruses (1×10$^{10}$ pfu/mouse), mice were sacrificed. Single cell suspension of splenocytes was made and pooled from three mice in each treatment group. Lymphocytes were isolated on a Ficoll-Hypague (Sigma Chemical, St. Louis, Mo.) gradient, washed twice, and then plated in 24-well plates at 2×10$^6$ cells/well. Lymphocytes were restimulated in vitro for 5 to 6 d with purified Adv-p53-E4 (WT) virus at MOI 1. Syngeneic 1422 cell line and CL4/SV40 cell line were used as target cells for C3H- and C57BL/6-originated effectors, respectively. Target cells were infected with WT virus at MOI 80 for 24 h. Uninfected cells were used as control target cells. CTL assay was performed by quantitatively measuring lactate dehydrogenase (LDH) release upon cell lysis, using the CytoTox 96 Assay kit (Promega, Madison, Wis.) according to the manufacturer's instruction. Results were calculated from the mean of quadruplicate samples and presented as the percent cytotoxicity for each effector:target cell ratio.

In vitro Studies. H1299 and A549 cells were plated at densities of 2×10$^6$ per 100-mm plate. The cells were then infected with recombinant adenoviral vectors at a multiplicity of infection (MOI) of 10 and grown at 37° C. Cells were harvested 48 h after infection and frozen at −20° C. until used for protein and luciferase assays.

Animal Studies. All animals were cared for according to the *Guide for the Care and Use of Laboratory Animals* (National Institutes of Health publication no. 85-23) and the institutional guidelines of The University of Texas, M. D. Anderson Cancer Center. In vivo infusion of adenoviral vectors into and subsequent tissue removal from Balb/c mice were done as described previously (Fang et al., 1994).

C57BL/6 mice and C3H/HeN were obtained from Charles River (Wilmington, Mass.). Five mice were used for each treatment group. Mice (8 to 10 wk old) were injected with 100 µl of 1×10$^{10}$ pfu adenoviruses in PBS by tail veil. Blood samples were collected from the tail at d 3, 7, 14, and 28 d postinjection, respectively. Serum samples were then assayed for serum glutamic-oxaloacetic transaminase (SGOT) and serum glutamine-pyruvate transaminase (SGPT) activities according to the standard test procedure. Animals were sacrificed with CO$_2$ at designed time. Livers were collected for pathological analysis and immunohistochemical analysis, and spleens for CTL assay.

SGOT and SGPT are serum transaminases that are used as measures of toxicity of drugs. SGOT (Serum glutamic-oxaloacetic transaminase), now known as AST (aspartate amino transferase) is not limited to liver. It is also released from muscle cells after strenuous excercise. Normally these enzymes are produced to break down toxins that enter the liver, but for overtly toxic drugs that damage the liver, lysis of the hepatocyes will release huge amounts of the enzyme into the serum, thus indicating toxicity. In humans, the normal range is 7–40 milliunits/ml. SGPT (serum glutamine-pyruvate transaminase), now known as ALT (alanine amino transferase), is another enzyme that is primarily localized to the liver, and thus another good indicator of liver toxicity. Normal range in humans is 5–35 milliunits/ml.

Statistical Analyses. Differences between treatment groups were assessed by ANOVA using SPSS software. P values less than 0.05 were considered significant.

Example 2

Construction of a Packaging Cell Line Expressing GAL4/VP16

A 293 cell line expressing GAL4 transactivating protein is required for generating an adenoviral vector whose E4 promoter is replaced by GAL4/TATA. The plasmids pM2/VP16 (containing a gene encoding the GAL4/VP16 fusion protein driven by SV40 early promoter) and pG5EC (containing a minimal promoter consisting of five consensus 17-mer GAL4 sites upstream from the adenovirus E1B TATA box) were obtained from Dr. I. Sadowski (University of British Columbia, Vancouver, Canada). Naive 293 cells were transfected by the CaPO$_4$ method with pM2/VP16 and pRSV/Neo, which encodes a neomycin-resistance gene driven by a Rous sarcoma virus-long terminal repeat (RSV-LTR), at a pM2/VP16:pRSV/Neo ratio of 10:1. The G418-resistant colonies were isolated and tested for their ability to transactivate GAL4/TATA promoter. The plasmid pG5EC, which contains a chloramphenicol acetyltransferase (CAT) gene driven by the GAL4/TATA promoter, was transfected into the G418-resistant cells, and CAT activity was determined. Three of 20 colonies were found to be capable of inducing CAT activity (FIG. 1). The duplication time, transfection efficiency, and viral production efficiency in these cells remained the same as in their parental 293 cells. One of these transformed cells (GV16) was then used to construct adenovirus vectors with E4 driven by GAL4/TATA.

Example 3

Construction of an Adenoviral Vector with E4 Driven by the GAL4/TATA Promoter

Figure 2C:
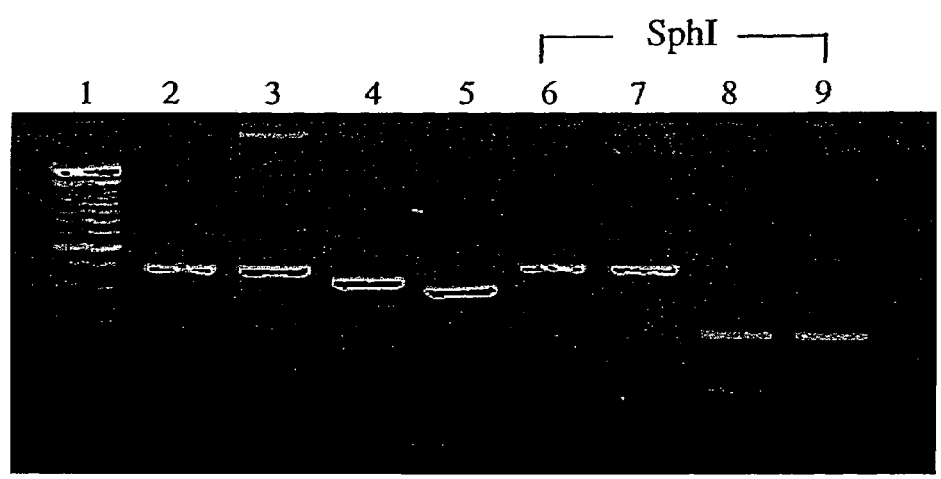
Figure 3B:
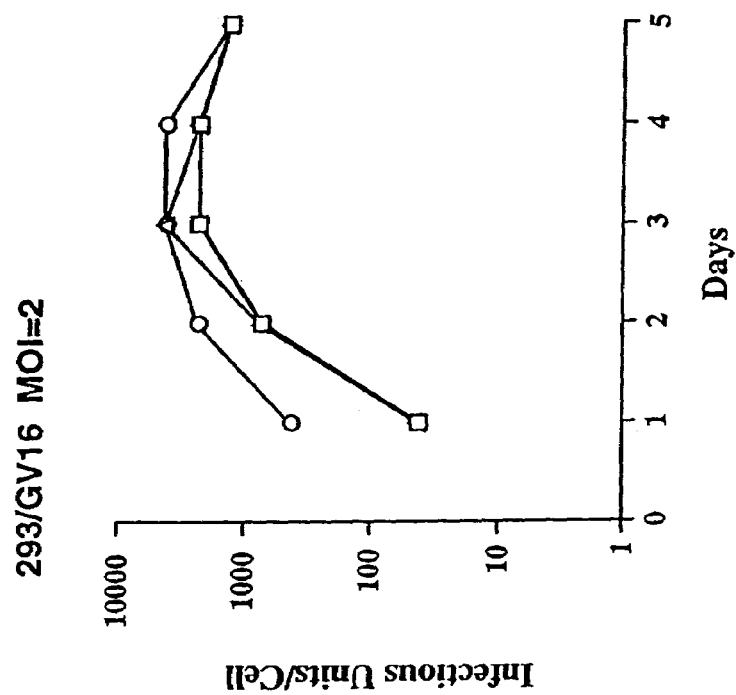
Figure 3A:
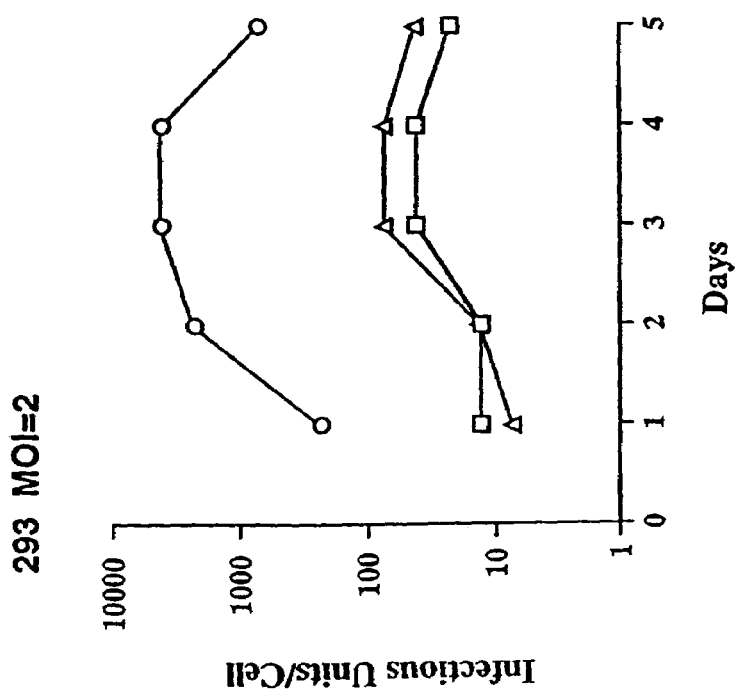
Figure 3D:
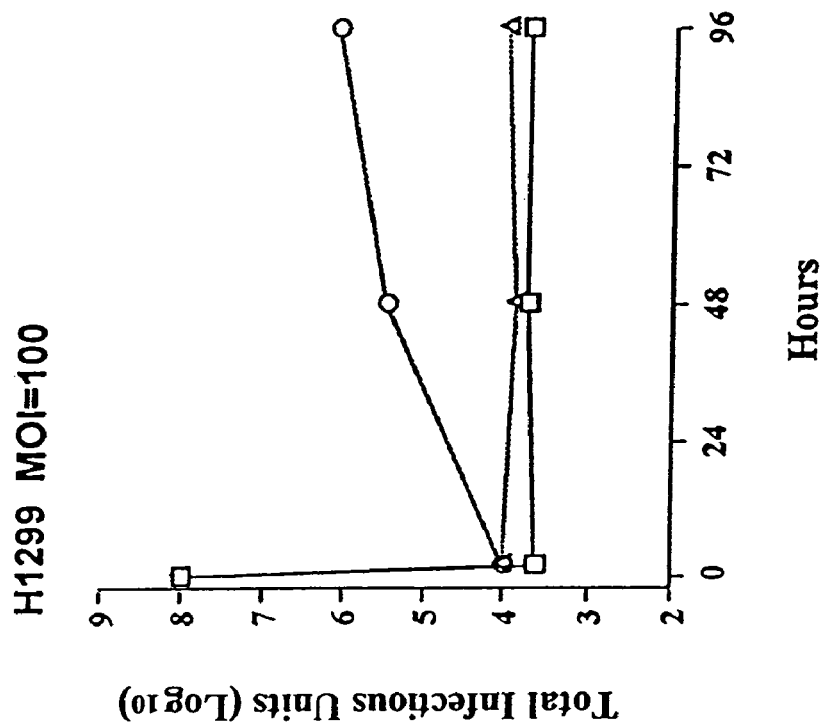
Figure 3C:
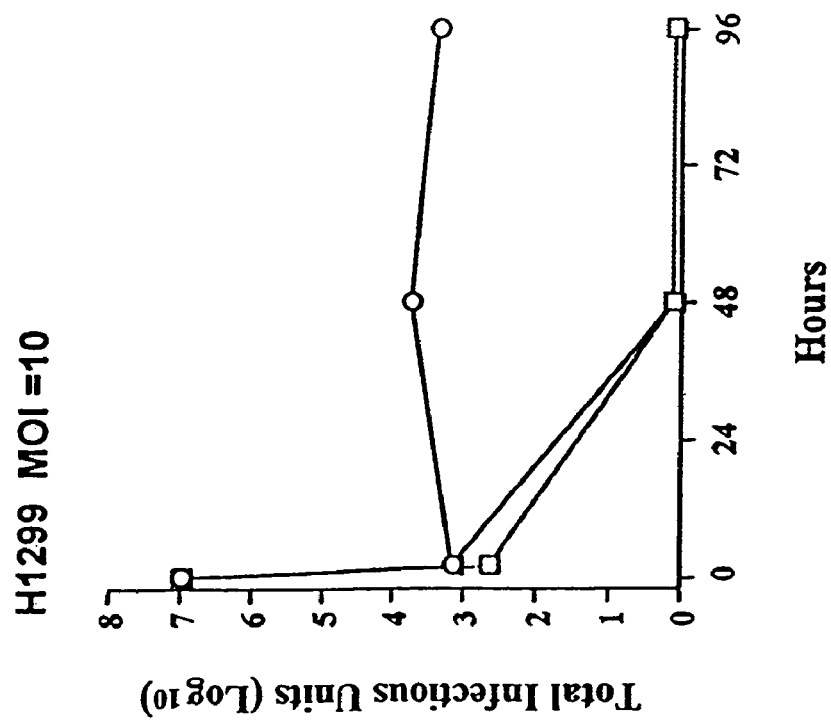

The inventors initially attempted to construct a vector in which GAL4/TATA would drive an E4 expression cassette inserted into the E1 region of the dl366 backbone (Halbert et al., 1985). This failed, however, because all of the viral preparations were contaminated with wild-type E1 or E4 virus. Several rounds of plaque purification did not solve the problem. This was attributed to the instability of the viral constructs, presumably due to the overlapping of E4 sequences in the E1 region with those in the dl366 backbone. In a second attempt, vectors were constructed by replacing the E4 promoter with GAL4/TATA in the original E4 region. In brief, two transfer plasmids (pBF7A and pBF7B) were constructed on a pNEB193 backbone (New England Biolabs, Beverly, Mass.). Both contained adenoviral sequences between map units 70 and 100 (FIG. 2A) and differed only in the right end of their terminal repeats. In pBF7A, the right-end fragment was cloned by digestion with MseI, which left 149 bp of the right-end inverted terminal repeats (ITR); in pBF7B, the right end was cloned by polymerase chain reaction (PCR™) and verified by subsequent sequencing of the cloned PCR™ product, to leave 117 bp of the right-end ITR. A recombinant adenoviral vector containing human factor IX (hFIX) cDNA driven by the RSV-LTR, Ad/RSV-hFIX, was constructed according to a method described previously (Fang et al., 1994). AdE4A/RSV-hFIX and AdE4B/RSV-hFIX were constructed by cotransfection of 293/GV16 cells with a 27-kb SrfI fragment from Ad/RSV-hFIX and either pBF7A (for AdE4A/RSV-hFIX) or pBF7B (for AdE4B/RSV-hFIX). All constructs were plaque-purified. The structures of these vector constructs (FIG. 2B) were confirmed by DNA analysis (FIG. 2C) and by functional assay for the presence of hFIX in the medium of the cultured cells transduced with the constructs.

Single plaques from each of the constructs were then expanded in 293/GV16 cells and purified through two cycles of CsCl gradient ultracentrifugation. Virus titers were measured by optical absorbance (1 A$_{260nm}$=10$^{12}$ particles/ml) and by plaque assay on cultured 293/GV16 and parental 293 cells. The viral concentration and total yield were similar for AdE4B/RSV-hFIX and Ad/RSV-hFIX, about twice as much as in AdE4A/RSV-hFIX. Plaque assays showed similar numbers of plaque-forming units (PFU) in 293 and 293/GV16 cells for Ad/RSV-hFIX, while for both AdE4A/RSV-hFIX and AdE4B/RSV-hFIX, the numbers of PFU were 10-fold lower in 293 cells than in 293/GV16 cells. The PFU obtained in 293/GV16 cells were used in the subsequent studies. All viral preparations were negative for contamination by the virus wild-type for E1 virus when assayed with a PCR™-based technique. AdE4A/RSV-hFIX and AdE4B/RSV-hFIX preparations were negative for contamination by virus wild-type for E4 when examined by PCR™ with a pair of primers that amplify adenoviral sequences stretching from base pair 35460 to 35935.

Example 4

Propagation of Recombinant Adenoviruses

The efficiency of viral propagation in 293 cells and 293/GV16 cells was tested by analyzing viral growth in the two cell lines. Cells (2.5×10$^5$/well) were seeded in 24-well plates and then infected with the various recombinant viruses at an MOI of 2. The cells were harvested at 1, 2, 3, 4, and 5 d after the viral inoculation, and the viruses were released by three cycles of freezing and thawing. The viral supernatant was then titrated in 293/GV16 cells by a tissue-culture-infective dose of 50% (TCID$_{50}$) (FIG. 3). The growth curve of Ad/RSV-hFIX was the same in both 293 cells and 293/GV16 cells, with a peak value of 2000 to 4000 viruses/cell being reached between d 2 and 4. The growth curve of AdE4A/RSV-hFIX and AdE4B/RSV-hFIX in 293/GV16 cells mimicked that of Ad/RSV-hFIX, with the peak value of 1000 to 4000 virus/cell being reached on d 3. The peak values of AdE4A/RSV-hFIX and AdE4B/RSV-hFIX in 293 cells were typically 1 to 2 orders of magnitude lower than that in the 293/GV16 cells. These results correlated with those of plaque assays, where the PFU for both AdE4A/RSV-hFIX and AdE4B/RSV-hFIX were reduced about 10-fold in naive 293 cells versus 293/GV16 cells. Together, these results suggested that the E4 functions of the two viral constructs with the promoter replacement were impaired but not completely abolished in the naive 293 cells.

Figure 4:
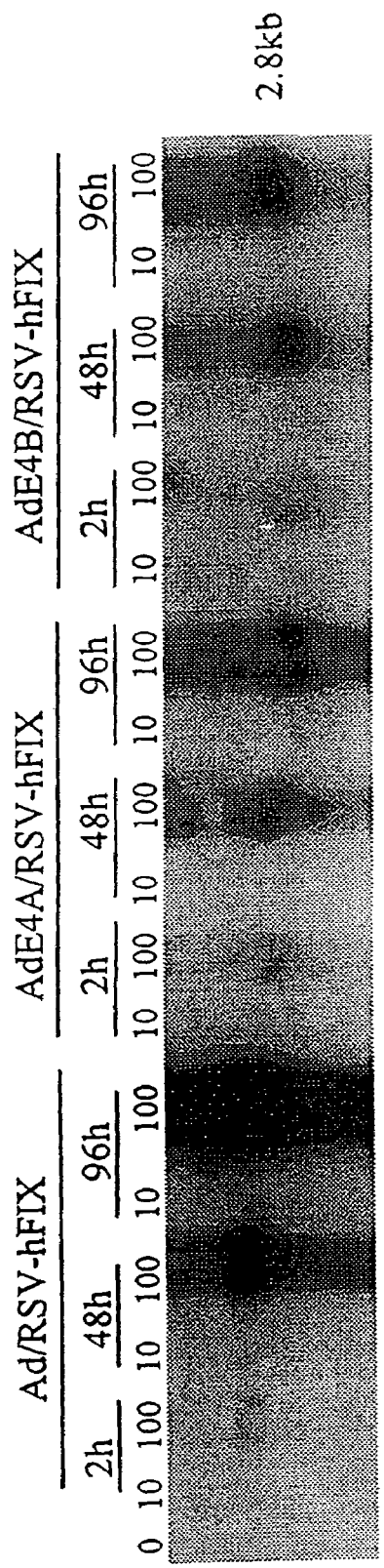
FIG. 4. Southern analysis of viral DNA in transfected H1299 cells. Cellular DNA (5 μg) was digested with ClaI and fractionated on 1% agarose gel. The viral constructs, h post-infection, and MOI used for infection are indicated above each lane.

Adenoviral replication in non-E1-transformed cells was tested in a human lung carcinoma cell line (H1299). Cells (1×10$^6$/well) were seeded in 6-well plates and then infected with the various recombinant viruses at MOI=10 or 100. The cells were harvested at 2, 48, and 96 h after viral inoculation. Cell lysate was titrated in 293/GV16 cells by determining the TCID$_{50}$ for the virus. At MOI 10, the total of infective viral particles remained unchanged during 2 h to 96 h postinfection in Ad/RSV-hFIX-infected cells. At the same MOI, the total of infectious viral particles dropped from about 10$^3$ to undetectable levels for both AdE4A/RSV-hFIX-infected cells and AdE4B/RSV-hFIX-infected cells (FIG. 3). At MOI 100, a significant increase in infectious viral particles was observed in cells infected with Ad/RSV-hFIX between 2 h and 96 h postinfection (FIG. 3). Meanwhile, at the same high MOI, the total infectious viral particles remained unchanged during the period of study in the cells infected with either AdE4A/RSV-hFIX or AdE4B/RSV-hFIX. These results were further supported by the analysis of DNA from the transfected cells. Southern blot analysis showed a dramatic increase in viral DNA in the cells transfected with Ad/RSV-hFIX at MOI 100 between 2 h and 96 h after viral infection (FIG. 4). At the same high MOI, the viral DNA increase was greatly retarded in the cells transfected with AdE4A/RSV-hFIX and AdE4B/RSV-hFIX. Southern blot and PCR™ analysis of the DNA from cells 96 h after infection with all three RSV-hFIX-containing viral constructs excluded the presence of E1+ virus, indicating that E1+ virus contamination did not likely contribute to viral replication in H1299 cells infected with Ad/RSV-hFIX. These results correlated well with previous observation by others that, at high MOI, E1-deleted adenovirus can replicate in non-E1-complementing cells (Shenk et al., 1980). These results also demonstrated that replacement of the E4 promoter with GAL4/TATA further diminished viral replication in non-E1-transformed cells.

Example 5

Viral Genes Expression in Cultured Human Carcinoma Cell Lines

To test E4 expression in the non-transformed cells, H1299 cells were infected with the three RSV-hFIX-containing viral constructs at MOI of 10 and 100. Mock-infected H1299 cells were used as negative controls while 293/GV16 cells infected at an MOI of 2 were used as positive controls. Preliminary studies showed that over 80% of H1299 cells were transduced at an MOI of 10. The cells were harvested 2 d after infection, and total RNA was isolated. Northern blot analysis showed that the E4 transcriptions in all the constructs tested were greatly reduced in H1299 cells versus 293/GV16 cells (FIG. 5), supporting the role of E1 in regulating E4 function (Shenk et al., 1980; Berk et al., 1979; Nevins, 1981). Nevertheless, at the high MOI (MOI=100), E4 transcription was quite substantial in H1299 cells transduced with Ad/RSV-hFIX. In contrast, at the same high MOI, E4 transcription was dramatically reduced in the H1299 cells transduced by viral constructs whose E4 promoter was replaced by GAL4/TATA, indicating that GAL4/TATA has much less transcriptional activity in non-E1-transformed cells than does the wild-type E4 promoter.

Figure 5:
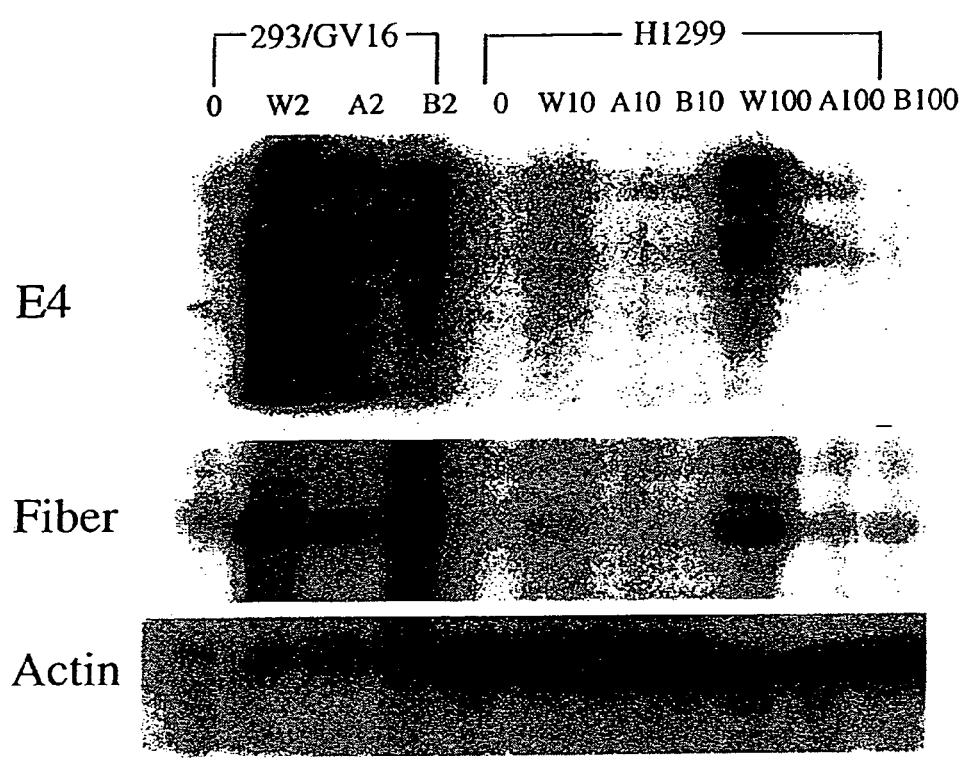
FIG. 5. Northern analysis of viral gene expression. Total RNA (20 μg) from transduced cells was loaded on a 1.2% agarose gel. Lane 0, mock infection; lane W, Ad/RSV-hFIX; lane A, AdE4A/RSV-hFIX; lane B, AdE4B/RSV-hFIX. The numbers next to W, A, and B represent MOIs.

The adenoviral E4 region encodes proteins required for late gene expression. Transcription rates for late genes in the cells infected with E4-deleted virus were reduced to 10% of those infected with the wild-type (Fang et al., 1994). Thus, diminution of E4 function by promoter replacement should reduce viral late gene expression. Expression of the viral fiber gene in H1299 cells was analyzed in the same northern blot used to detect E4 mRNA (FIG. 5). Such expression correlated with that of E4. Moreover, a substantial amount of fiber transcript was detected only in H1299 cells transduced by the vector with a wild-type E4 promoter at an MOI of 100. In contrast, fiber expression in H1299 cells transduced by the vectors with a replaced E4 promoter was greatly diminished as compared with that of cells transduced by vectors with wild-type E4.

Hexon gene expression from the three RSV-hFIX containing vectors was determined in two human lung carcinoma cell lines, H1299 and A549. Cells were transduced with Ad/RSV-hFIX, AdE4A/RSV-hFIX, or AdE4B/RSV-hFIX. Hexons (green) were visualized using FITC-labeled polyclonal goat antibody. The cells were infected at MOIs of 0, 10, and 100 and then cultured at 37° C. for 2 d. Hexon protein was detected by staining with an FITC-labeled antibody that specifically recognizes adenoviral hexon. At MOI 10, about 10% of H1299 cells and less than 1% of A549 cells transduced with Ad/RSV-hFIX were FITC positive, consistent with the previous observation that adenovirus-mediated transduction efficiency is higher in H1299 cells than in A549 cells. About 80% of H1299 cells and about 10% of A549 cells were transduced at MOI 10. In comparison, neither cell line was FITC positive when transduced with AdE4A/RSV-hFIX or AdE4B/RSV-hFIX at MOI 10. At MOI 100, about 50% of H1299 cells and 10–25% of A549 cells transduced with Ad/RSV-hFIX were FITC positive. In comparison, only 1–5% of H1299 cells were positive when transduced with AdE4A/RSV-hFIX or AdE4B/RSV-hFIX, while A549 cells transduced with AdE4A/RSV-hFIX or AdE4B/RSV-hFIX remained FITC negative.

Example 6

Expression of Heterologous DNA

Levels of hFIX in the culture media of transduced cells reflected the efficiency of gene delivery with the vectors. These levels were determined by ELISA (Table 3). No detectable hFIX was found in media from mock-infected cells or from cells transduced with Ad/CMV-LacZ. Human FIX levels in media from A549 cells transduced with Ad/RSV-hFIX were about twice those in media from cells transduced with AdE4A/RSV-hFIX or AdE4B/RSV-hFIX at MOI 100. At MOI 10, hFIX was undetectable in the media from A549 cells transduced with any of the three RSV-hFIX-containing constructs. In contrast, hFIX levels in the media from H1299 cells transduced with the same three RSV-hFIX-containing constructs were equivalent at all MOI tested. Together, these results demonstrated that the transduction efficiencies of the three RSV-hFIX-containing vectors were similar in the two human cell lines tested, indicating in turn that reduction of viral gene expression in cells transduced with AdE4A/RSV-hFIX or AdE4B/RSV-hFIX was not caused by decreased transduction efficiencies.

TABLE 3

Human factor IX in the media of cultured cells transduced with recombinant adenoviral vectors containing RSV-hFIX

| Cells | Vectors | MOI | hFIX (ng)* |
|---|---|---|---|
| H1299 | Ad/RSV-hFIX 10 | 10 | 169.9 ± 7.6 |
| | AdE4A/RSV-hFIX | 10 | 224.2 ± 27.1 |
| | AdE4B/RSV-hFIX | 10 | 116.4 ± 17.6 |
| | Ad/CMV-LacZ | 10 | 0 |
| | Ad/RSV-hFIX 100 | 100 | 293.4 ± 45.3 |
| | AdE4A/RSV-hFIX | 100 | 298.9 ± 46.4 |
| | AdE4B/RSV-hFIX | 100 | 301.1 ± 44.3 |
| | Ad/CMV-LacZ | 100 | 0 |
| A549 | Ad/RSV-hFIX 100 | 100 | 136.2 ± 45.7 |
| | AdE4A/RSV-hFIX | 100 | 67.9 ± 4.7 |
| | AdE4B/RSV-hFIX | 100 | 61.55 ± 9.0 |
| | Ad/CMV-LacZ | 100 | 0 |

*hFIX levels represent mean ± s.d. in duplicate studies; they are presented as the total hFIX yields from $1 \times 10^5$ cells after 48 h of incubation at the indicated MOIs.

Example 7

Evaluation of GAL4/TATA In vivo: Vector Construction

Figure 6:
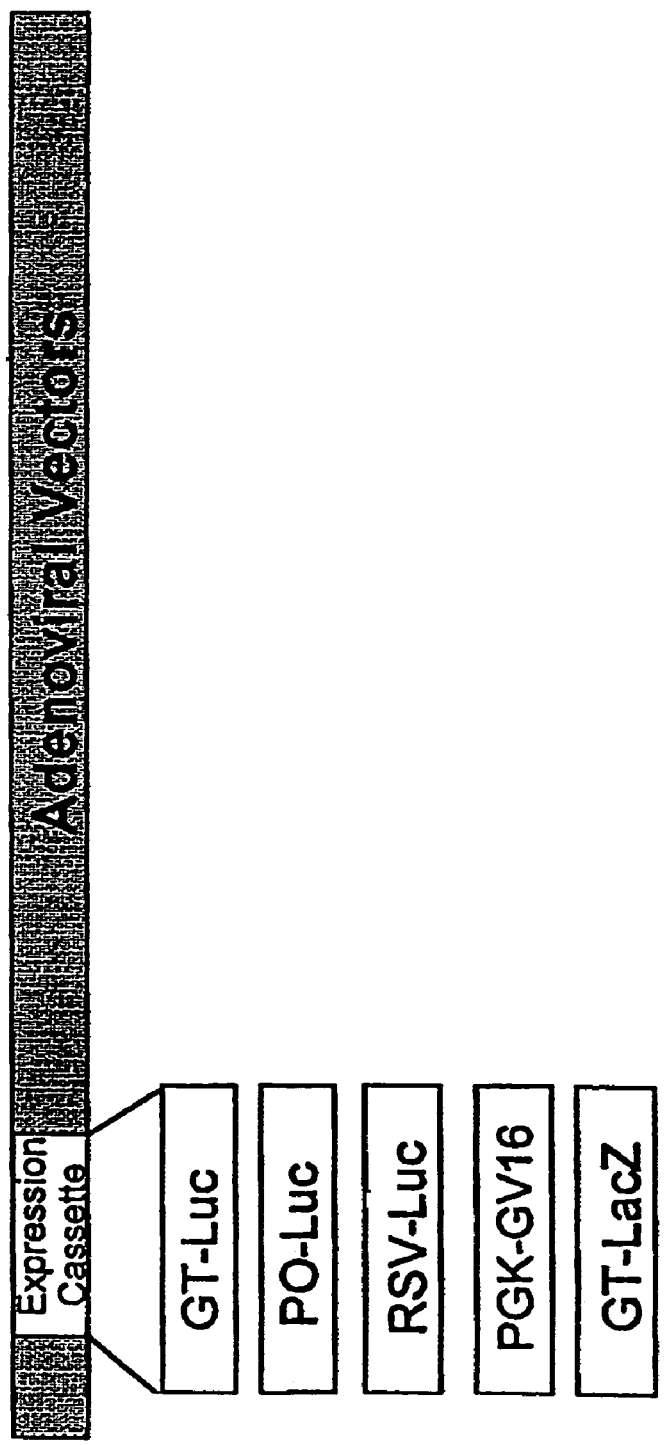
FIG. 6. Adenoviral vectors used in this study. In all vectors, the expression cassette is inserted in the adenoviral E1 region. GT=GAL4/TATA promoter; Luc=luciferase cDNA; PO=no promoter present; RSV=Rous sarcoma virus long terminal repeat; PGK=3-phosphoglycerate kinase gene promoter; GV16=cDNA for GAL4/VP16 fusion protein; LacZ=*Escherichia coli* LacZ gene. All expression cassettes are oriented from right to left and contain polyadenylation sequences (pA) from bovine growth hormone gene, except for RSV-Luc, which is described elsewhere (Zhang et al., 1994).

In this example, luciferase was used as a reporter to evaluate GAL4/TATA promoter activity in vivo because firefly luciferase assays are sensitive enough to detect even trace levels of promoter activity. Several adenoviral vectors containing the luciferase reporter gene were constructed and used in in vitro and in vivo studies (FIG. 6). A vector containing only the luciferase gene and a poly(A) signal sequence but no promoter (Ad/PO-Luc), was also constructed and used as a negative control; a vector containing luciferase cDNA driven by the RSV-LTR (Ad/RSV-Luc) was used as a positive control. To induce GAL4/TATA activities in vitro and in vivo, an adenoviral vector expressing a GAL4/VP16 fusion protein (GV16) driven by a housekeeping promoter (PGK) was constructed. All viral constructs were purified by two cycles of ultracentrifugation on a CsCl gradient. Viral titers were determined by $TCID_{50}$ assay. All viral preparations were tested for $E1^+$ adenovirus contamination by PCR™ (Fang et al., 1996) and for cross-contamination by Ad/RSV-Luc by PCR™ using primers located in RSV-LTR and luciferase cDNA. No contamination was detected in viral preparations used in this example.

Example 8

GAL4/TATA Activities in Cultured Human Cell Lines

Established human lung carcinoma cell lines H1299 and A549 were used to determine basal activity levels of GAL4/TATA in the adenoviral backbone. In brief, cells were infected with Ad/GT-Luc, Ad/PO-Luc, Ad/RSV-Luc, and Ad/GT-LacZ at MOI 10. Preliminary studies showed that over 80% of the H1299 cells and over 20% of the A549 cells were transduced at MOI 10. Cells were then harvested 48 h after infection.

Figures 7A, 7B:
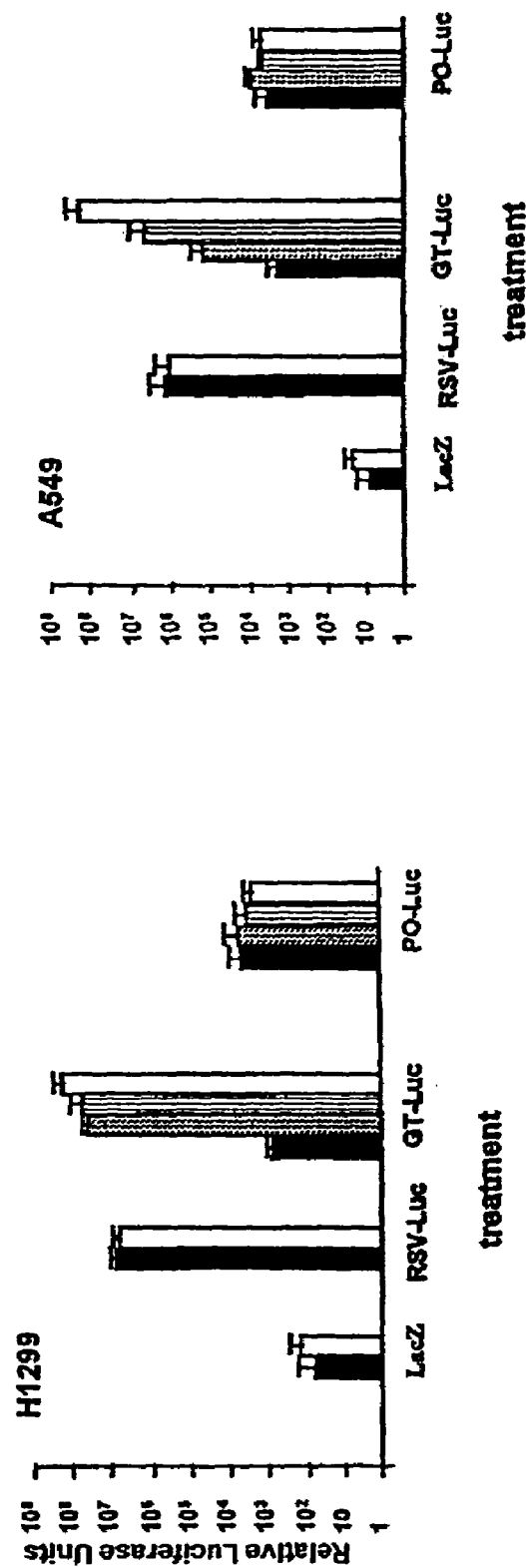
FIG. 7A and FIG. 7B. In vitro evaluation of GAL4/TATA promoter activity. H1299 (FIG. 7A) and A549 (FIG. 7B) cells were infected with each virus at MOI 10 as indicated at the bottom of bars. The luciferase activities were determined as described in the text and expressed as light units/μg of cellular protein. Each value represents mean+standard deviation of two duplicated assays. Solid bar indicates virus alone; striped bar indicates virus plus 1/1000 Ad/PGK-GV16; dotted bar indicates virus plus 1/100 Ad/PGK-GV16; open bar indicates virus plus 1/10 Ad/PGK-GV16.

Mock-infected cells were used as background controls. Luciferase activity was measured and expressed as relative light units/μg of cellular protein (FIG. 7). In both H1299 and A549 cells, the luciferase activity was significantly higher in cells infected with Ad/GT-Luc or Ad/PO-Luc than in cells infected with Ad/GT-LacZ ($P<0.05$). These results are consistent with earlier reports of low basal activity of GAL4/TATA-driven reporters in HeLa and CHO cells (Sadowski et al., 1992). Nevertheless, since the same basal level of luciferase activity was observed in constructs without promoters (Ad/PO-Luc), the role of the GAL4/TATA promoter in this basal activity is not yet clear.

Example 9

In Vitro Induction of GAL4/TATA Activities

As reported previously by others, expression of the GAL4-VP16 fusion protein via plasmid cotransfection increases the in vivo induction of GAL4/TATA activity at least 1200-fold (Sadowski et al., 1992). To test whether the induction of GAL4/TATA activities might be similarly induced through adenovirally-mediated gene codelivery, H1299 and A549 cells were infected at MOI 10 with a mixture of Ad/GT-Luc and Ad/PGY-GV16 in ratios of 1000:1, 100:1, and 10:1. Luciferase activities were then determined 48 h postinfection. As the ratio moved from 1000:1 to 10:1 the luciferase activities increased about $1 \times 10^4$ to $4.1 \times 10^4$ fold in H1299 cells and 7.5 to $9 \times 10^4$ fold in A549 cells. In contrast, no change in luciferase activity was observed in cells infected with mixtures of Ad/PO-Luc and Ad/PGK-GV16 at the same ratios. Moreover, mixing Ad/GT-LacZ or Ad/RSV-Luc with Ad/PGK at a ratio of 10:1 had no significant effect on luciferase activities either. Thus, induction by adenovirally-mediated gene codelivery appears to be dose dependent and highly effective. In addition, the difference between the two cell lines in their response to the induction may be reflected by their sensitivity to adenoviral infections (Fang et al., 1997).

Example 10

Basal GAL4/TATA Promoter Activity in Adenoviral Vectors In Vivo in the Balb/c Animal Model To determine the basal level of GAL4/TATA promoter activity, 6- to 8-wk-old female Balb/c mice were infused through the tail vein with either Ad/RSV-Luc, Ad/PO-Luc, Ad/GT-Luc, or Ad/GT-LacZ at a dose of $1 \times 10^9$ per mouse. Mice infused with PBS alone served as negative controls. All mice were killed 2 d after infusion after which liver, spleen, lung, kidney, intestine, ovary, and brain were collected and homogenized for luciferase and protein assays. Luciferase activities were readily detected in liver, lung, spleen, heart, ovary, and kidney of mice infused with Ad/RSV-Luc. No or only background levels of luciferase activities were detected in all organs tested in animals infused with other viral constructs, including those infused with Ad/GT-Luc (FIG. 8A through FIG. 8H). Together, these results demonstrated that the GAL4/TATA promoter was not active in vivo in the adenoviral backbone.

Example 11

In Vivo Induction of GAL4/TATA Promoter Activity

To determine whether GAL4/TATA promoter activity could be induced in vivo by adenovirally-mediated gene codelivery as demonstrated in the in vitro studies, a group of Balb/c mice infused with $1 \times 10^9$ pfu of vector mixtures containing Ad/GT-Luc and Ad/PGK-GV16 (10:1) was included in the animal study mentioned above. Mice infused with Ad/RSV-Luc plus Ad/PGK-GV16 or Ad/PO-Luc plus Ad/PGK-GV16 at the same dose and ratio were used as controls. While no luciferase activity was detected in mice infused with Ad/GT-Luc alone, luciferase activities were dramatically induced in all organs of mice treated with Ad/GT-Luc plus Ad/PGK-GV16. The induction ranged from $1.4 \times 10^4$ fold in brain to $9.3 \times 10^6$ in liver. No induction was found in animals treated with Ad/PO-Luc plus Ad/PGK-GV16, and no significant differences in luciferase activities were observed between animals infused with Ad/RSV-Luc alone or Ad/RSV-Luc plus Ad/PGK-Luc. Thus, these results demonstrated that in vivo induction of GAL4/TATA by GAL4/VP16 through adenovirally-mediated gene codelivery is highly specific and efficient. These results also ruled out loss of vector infectivity as the reason why luciferase activity was undetectable in animals treated with Ad/GT-Luc alone.

Example 12

Diminished Viral Gene Replication and Expression In Vitro

The potential for diminishing viral gene replication and expression by E4 promoter replacement has been evaluated in human cancer cell line H1299 and lung carcinoma cell line A549. Adenoviral replication was analyzed in adenovirus infected H1299 cell line by Southern blot using the E4 ORF6 DNA (910 bp) fragment as a probe (FIG. 9A). At MOI of 10, the viral DNA remained unchanged from d 1 to d 7 postinfection for all the vectors. At MOI Of 80, the viral DNA increased significantly in cells infected by BG and WT from d 1 to d 7 postinfection, but the viral DNA production was dramatically reduced (FIG. 9A) and was 20- to 25-fold lower in the G4-infected cells than that in BG- and WT-transfected cells at the same MOI (FIG. 9B).

Figure 10A:
FIG. 10A, FIG. 10B and FIG. 10C. Expression of viral hexon and human p53 proteins in recombinant adenovirus-transfected human cancer cell lines by Western analysis. 20 μg of total crude protein extract was loaded on each lane.
Figure 10B:
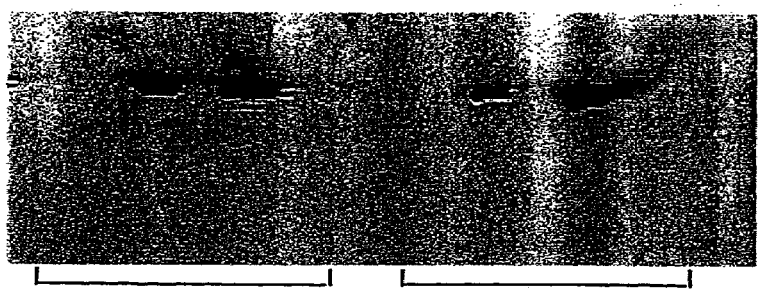
Figure 10C:
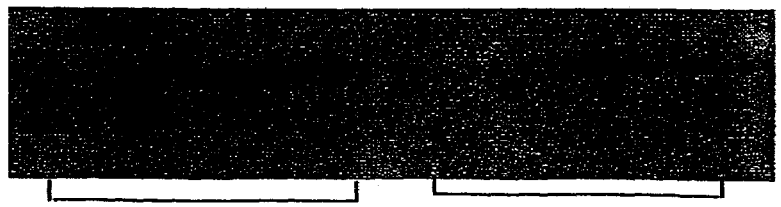

Western blot using a mouse anti-Ad5 hexon protein monoclonal antibody was carried to investigate the effect of inactivated E4 on the expression of the viral late gene (FIG. 10A). A consistent level of hexon protein was observed in both BG- and WT-infected H1299 cells (at MOI 10; FIG. 10A) and A549 cells (at MOI 50; FIG. 10B) on d 1 and d 7 postinfection but no hexon protein was detected in G4-infected cells. These results demonstrated that inactivation of E4 promoter diminished viral replication and viral late gene expression in these human carcinoma cells.

Example 13

Expression of p53 Gene In Vitro and its Effects on Tumor Cell Growth and Apoptosis Western blot with a mouse anti-human p53 monoclonal antibody was carried out to analyze vector-mediated expression of the p53 gene in human carcinoma cell lines (FIG. 10B). The same high level of p53 protein were observed in both G4 and WT-infected H1299 cells at a MOI Of 10 throughout the time course of infection (from d 1 to d 7), demonstrating that the E4 inactivation did not affect the efficiency of transgene expression in vitro.

Figure 11A:
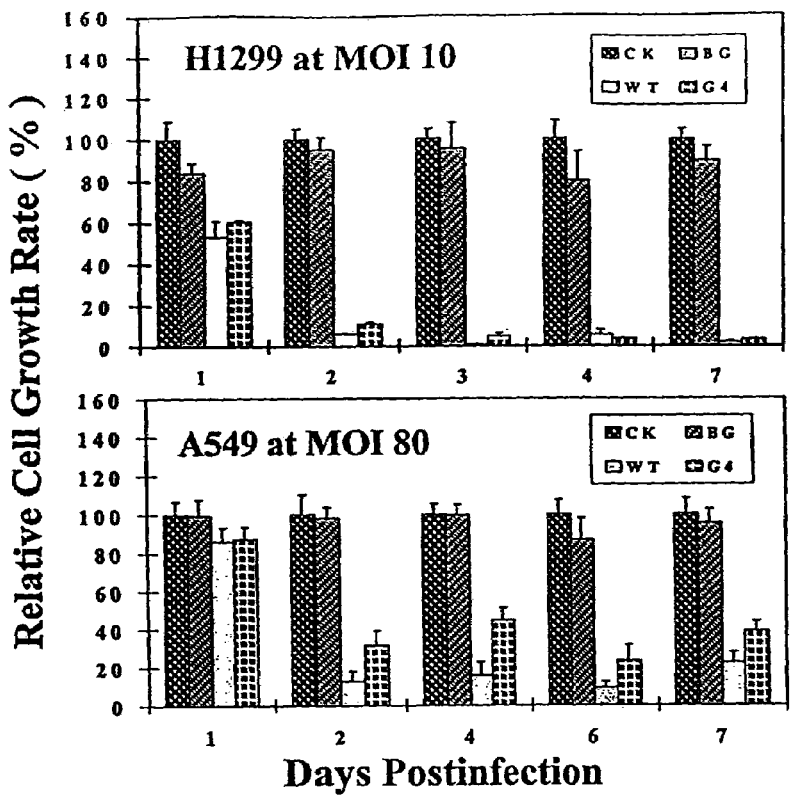
FIG. 11A, FIG. 11B and FIG. 11C. Inhibition of cell growth and apoptosis in human cancer cells transfected by recombinant adenoviruses.
Figure 11B:
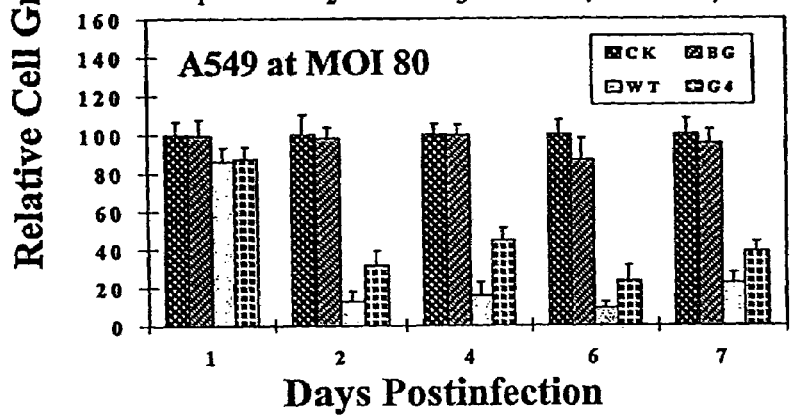
Figure 11C:
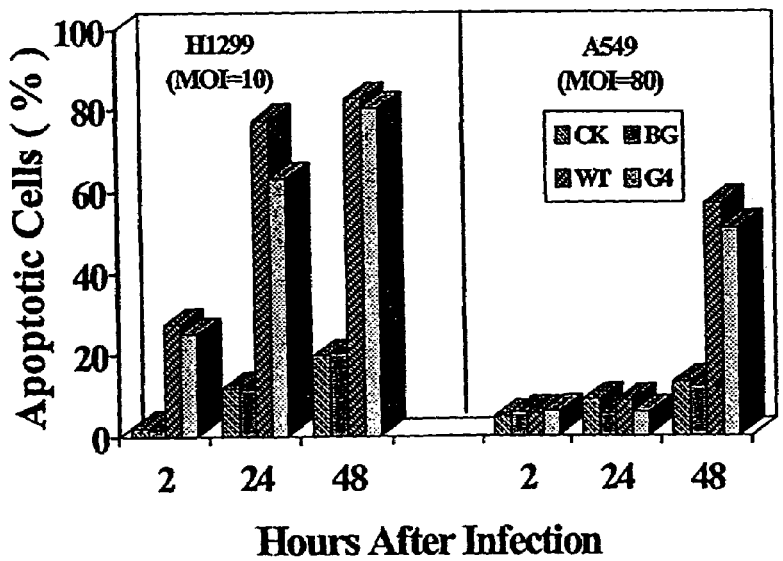

To test the ability of recombinant adenoviruses carrying the human p53 gene to inhibit cancer cell growth, different doses of viruses were used to infect a human lung cancer cell line, H1299 (with intrinsically deleted p53) and a human lung carcinoma cell line, A549 (with wild type p53) (FIG. 11A). Cell growth rate was determined by MTT staining. Both WT and G4 constructs inhibited H1299 cell growth dramatically at a MOI of 10, at d 1, 2, 3, 4 and 7 postinfection, compared to the PBS (CK) and BG controls. The pattern and extend of growth inhibition by WT and G4 viruses are similar, indicating a similar level of p53 gene function. Both WT and G4 constructs also inhibited A549 (wild type p53) cell growth at a MOI Of 80 through the time course of infection, but G4 showed a lower level (30 to 40% lower) of inhibition than WT construct, suggesting a reduced cytotoxicity of the E4 inactivated vector in vitro.

p53 gene-mediated cell growth inhibition is realized mainly through the pathway of induced apoptosis. Apoptosis of virus-infected H1299 cells was determined by flow cytometry with TUNEL staining (FIG. 11B). G4-infected H1299 cells demonstrated the similar level of apoptosis as the WT-infected cells, indicating a similar mechanism of transgene function in both constructs.

Example 14

Diminished Viral Protein Expression In Vivo

To determine the effect of E4 inactivation on expression of viral proteins in vivo, the expression of viral hexon protein in vector-injected mouse livers was analyzed by in situ immunohistochemistry staining using mouse anti-Ad5 hexon monoclonal antibody. Frozen mouse liver tissue sections were analyzed by immunohistochemistry stain with a FITC-conjugated mouse anti-adenovirus hexon monoclonal antibody and with 0.025% Evane Blue as counterstain. Immunocomplex was examined under a fluorescence microscope with a dual light (red and green) filter. Mice were sacrificed at d postinjection as indicated. The liver tissues were prepared from mice injected with PBS, G4, BG, and WT, respectively. Expression of viral hexon protein was observed in both BG and WT injected mice after 3, 7, and 14 d, but hardly detectable in G4-treated mice. These observations indicate that the inactivation of the E4 promoter efficiently diminished the late viral protein expression in vivo.

Example 15

Reduced Toxicity in Mouse Liver by E4 Promoter Inactivation

Further investigations were performed as to whether a vector with an extended deletion in E1–E3 and inactivation of E4 promoter reduces toxicity. The inventors used both C3H and C57BL/6 mice for studying the toxicity induced by tail vein injection of BG, WT, G4, EW (E1$^-$ empty vector Adv-E4, without modification of E4), and EG (E1$^-$ empty vector Adv-GAL4, with modification of E4) Ad constructs with PBS as control. Vector-induced liver toxicity or damage was evaluated by analyzing the serum transaminases, SGOT (FIG. 12A, FIG. 12C) and SGPT (FIG. 12B, FIG. 12D) activities. In all cases, there were significant decreases in (30 to 50% lower) SGOT and SGPT activities in EV/G4- and G4-treated C3H (FIG. 12A, FIG. 12B) and C57BL/6 (FIG. 12C, FIG. 12D) mice, compared to those in EV/WT and WT-treated mice, respectively, during 3, 7 and 14 d postinjection.

The adenovirus-induced pathologic changes in liver tissues were evaluated by examination of HE-stained paraffin sections with a scoring system which quantified hepatocellular necrosis and degeneration, intralobular and periportal intimation, and apoptosis (FIG. 13). Virus-induced pathology in C57BL mice were dominated by the lobular and portal intimation (FIG. 13B, FIG. 13C) and the hepatocellular necrosis (FIG. 13A), with no significant lesion at d 3, marked inflammatory response at d 7 and then decreased to moderate at d 14 postinjection. The overall response of C57BL mice to G4 infection was notably reduced compared with WT infection (FIG. 13A, FIG. 13B, FIG. 13C). The apoptosis was noticed mild at d 3 in hepatocytes infected with all three vectors and moderately increased responses at d 7 and 14 in WT- and G4-treated mice (FIG. 13F). In C3H mice, the virus- and transgene-induced apoptosis was the dominant pathology, with sever response in WT infected mice at d 7 (FIG. 13F); while the inflammatory responses in C3H mice was similar to those in C57BL mice at d 7, the effect lasted longer and higher in WT infected mice than in G4- and BG-infected ones (FIG. 13B, FIG. 13C). The overall pathologic responses of C3H mice to G4 vector was appeared decreased compared to WT vector (FIG. 13A, FIG. 13B, FIG. 13C, FIG. 13D, FIG. 13E, FIG. 13F).

Example 16

Prolonged p53 Gene Expression In Vivo

In situ immunohistochemstry staining of virus-injected mouse liver crytosections was performed to analyze the vector-mediated expression and persistence of p53 gene in vivo. Frozen mouse liver tissue sections were analyzed by immunohistochemistry stain with a FITC-conjugated mouse anti-adenovirus hexon monoclonal antibody and with 0.025% Evane Blue as counterstain. Immunocomplex was examined under a fluorescence microscope with a dual light (red and green) filter. Expression of p53 gene was observed similar in both WT- and G4-injected C57BL/6 mouse livers after 7 and 14 d, although a slightly higher level of expression was observed in G4-treated mice than those of WT-treated mice. The p53 gene expression was still detectable in G4-treated C57BL/6 mice 10 wk after injection, but barely notable in WT-treated mice, suggesting that a prolonged and stabilized transgene expression could be achieved in the E4 inactivated vector, by reduced viral protein production and host immune response.

Example 17

Attenuated CTL Response by E4 Inactivation

The response of MHC class I-restricted cytotoxic T lymphocytes (CTL) to adenoviral vectors and heterologous transgene has been suggested and shown to have importance in limiting duration of transgene expression and inducing tissue toxicity. It has been predicted that adenovirus vectors with diminished viral gene expression would reduce cellular immunity and prolong transgene expression.

Substantial efforts have been made to develop less immunogenic vectors by introduction of additional modifications in E2, E4 and all viral coding genes (Engelhardt et al., 1994; Krougliak and Graham, 1995; Lieber et al., 1996; Gao et al., 1996; Hardy et al., 1997; Dedieu et al., 1997; Morral et al., 1997). These efforts were based on the hypothesis that the diminished expression of late viral proteins would lead to the reduced immunogenicity and thus prevent the destruction of the transduced cells and prolong transgene expression.

Figures 14A, 14B:
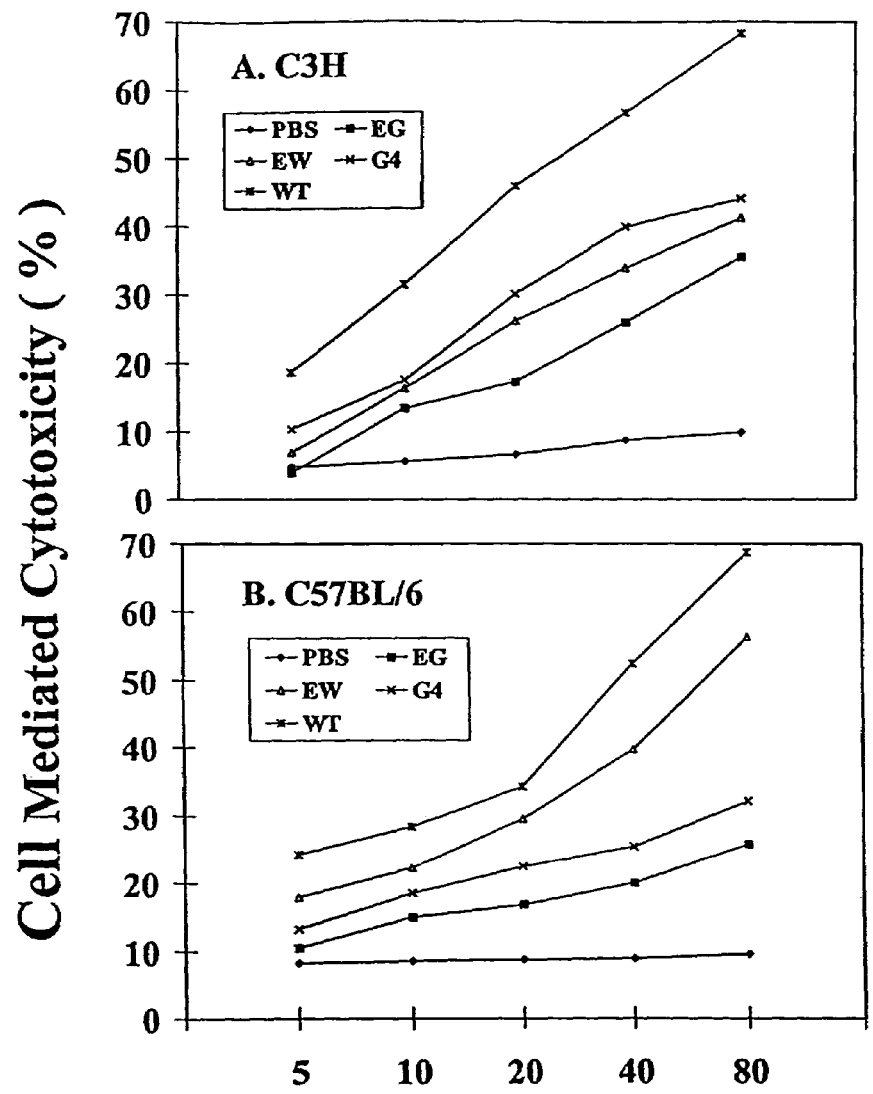

In this example, the CTL responses to the viral protein and transgenes in both virus-injected C3H and C57BL/6 mice were analyzed to evaluate the effect of E4 inactivation on the vector induced immunogenicity (FIG. 14A and FIG. 14B). Although CTL activity was noted in lymphocytes from both C3H and C57bL/6 mice treated with all the adenovirus constructs, the E4 inactivated empty vector EG showed the lowest CTL response. The inventors also noticed the different CTL responses between C3H and C57BL/6 mice. In C3H mice, both the transgene-carrying vector WT- and G4-immunized mice showed a higher CTL response than the empty vector EV- and EG-treated mice, suggesting that the transgene dominated the immune response. While in C57BL/6 mice, the total CTL activities were 2- to 3-fold higher in animals that treated with WT and EW than those treated with EG, and 3- to 5-fold higher than mice treated with EG, respectively, suggesting that the diminished viral gene expression contribute mainly to the reduced cellular immunity in these animals. The observed CTL responses are well correlated with the pathological figures and the production of the late viral proteins in vector-injected mice. These observations also are consistent with reports showing that the different genetic background in mice and the different backbone structure and transgene carried in adenovirus vectors resulted in apparent discrepancies in immune responses (Gao et al., 1996; Song et al., 1997; Sparer et al., 1997; Kaplan and Smith, 1997; Dedieu et al., 1997).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Anderson et al., U.S. Pat. No. 5,399,346, 1995.
Arap et al., *Cancer Res.*, 55:1351–1354, 1995.
Baichwal and Sugden, In: *Gene transfer*, Kucherlapati R, ed., New York: Plenum Press, pp. 117–148, 1986.
Bedzyk et al., *J. Biol. Chem.*, 265:18615, 1990.
Bennett et al., *Invest. Opthal. and Vis. Sci.*, 35:2535–2541, 1994.
Benvenisty and Neshif, *Proc. Nat. Acad. Sci. USA*, 83:9551–9555, 1986.
Berk et al., *Cell*, 17:935–944, 1979.
Brand and Perrimon, *Development*, 118:401–415, 1993.
Braselmann et al., *Proc. Natl. Acad. Sci. USA*, 90:1657–1661, 1993.
Bussemakers et, al.; *Cancer Res.*, 52:2916–2922, 1992.
Caldas et al., *Nat. Genet.*, 8:27–32, 1994.
Capaldi et al., *Biochem. Biophy. Res. Comm.*, 74 (2):425–433, 1977.
Casey et al., *Oncogene*, 6:1791–1797, 1991.
Chaudhary et al., *Proc. Natl. Acad. Sci.*, 87:9491, 1990.
Chen and Okayama, *Mol. Cell Biol.*, 7:2745–2752, 1987.
Cheng et al., *Cancer Res.*, 54:5547–5551, 1994.
Cheung et al., *J. Biol. Chem.*, 268:24303–24310, 1993a.
Cheung et al., *J. Biol. Chem.*, 268:6139–6146, 1993b.
Cheung et al., *Biochem. J.*, 295:427–435, 1993c.
Chiao et al., *Cancer Metastasis Rev.*, 9:63–80, 1990.
Couch et al., *Am. Rev. Resp. Dis.*, 88:394–403, 1963.
Coupar et al., *Gene*, 68:1–10, 1988.
Dai et al., *Proc. Natl. Acad. Sci. USA*, 92:1401–1405, 1995.
Dedieu et al., *J. of Virol.*, 71:4626–37, 1997.
Dubensky et al., *Proc. Nat. Acad. Sci. USA*, 81:7529–7533, 1984.
Edelman and Crossin, *Annu. Rev. Biochem.*, 60:155–190, 1991.
Edelman, *Annu. Rev. Biochem.*, 54:135–169, 1985.
Englehardt et al, *Human Gene Therapy*, 5:1217–1229, 1994.
Ensinger and Ginsberg, *J. of Virol.*, 10:328–339, 1972.
Fang et al., *J. of Virol.*, 71:4798–4803, 1997.
Fang et al., *Gene Ther.*, 3:217–222, 1996.
Fang et al., *Gene Ther.*, 1:247–254, 1994.
Fechheimer et al., *Proc. Natl. Acad. Sci. USA*, 84:8463–8467, 1987.
Fenner, In: *The Biology of Animal Viruses*, Fenner, McAuslan, ed., New York: 543–586, 1974.
Ferkol et al., *FASEB J.*, 7:1081–1091, 1993.
Fraley et al., *Proc. Natl. Acad. Sci. USA*, 76:3348–3352, 1979.
Freshner, "Animal Cell Culture: a Practical Approach", Second Edition, Oxford/New York, IRL Press, Oxford University Press, 1992.
Frixen et al., *J. Cell Biol.*, 113:173–185, 1991.
Gao et al, *J. of Virol.*, 70:8934–43, 1996.
Ghosh and Bachhawat, In: *Liver diseases, targeted diagnosis and therapy using specific receptors and ligands*, Wu G, Wu C ed., New York: Marcel Dekker, pp. 87–104, 1991.
Giancotti and Ruoslahti, *Cell*, 60:849–859, 1990.
Gomez-Foix et al., *J. Biol. Chem.*, 267:25129–25134, 1992.
Gopal, *Mol. Cell Biol.*, 5:1188–1190, 1985.
Gorziglia et al, *J. of Virol.*, 70:4173–4178, 1996.
Graham et al, *J. of General Virol.*, 36:59–74, 1977.
Graham and Prevec, In: *Methods in Molecular Biology: Gene Transfer and Expression Protocols* 7, Murray, E. J. Editors. Clifton, N J: Humana Press, 109–128 and 205–225, 1991.
Graham and Van Der Eb, *Virol.*, 52;456–467, 1973.
Grunhaus and Horwitz, *Seminar in Virol.*, 3:237–252, 1992.
Guo et al., *Gene Ther.*, 3:802–810, 1996.
Halbert et al., *J. Virol.*, 56:250–257, 1985.
Hardy et al., *J. of Virol.*, 71:1842–1849, 1997.

Harland and Weintraub, *J. Cell Biol.*, 101:1094–1099, 1985.
Hay et al., *J. of Mol. Biol.*, 175:493–510, 1984.
Hearing et al., *J. of Virol.*, 67:2555–2558, 1987.
Hermonat and Muzycska, *Proc. Nat. Acad. Sci. USA*, 81:6466–6470, 1984.
Herz and Gerard, *Proc. Natl. Acad. Sci. USA*, 90:2812–2816, 1993.
Hollestein et al., *Science*, 253:49–53, 1991.
Hornbeck, "Antibody detection and preparation," In: *Current protocols in immunology*, Coligan, J. E., et al. Editors. New York: John Wiley, 2.1.1–2.1.22, 1994.
Hussussian et al., *Nature Genetics*, 15–21, 1994.
Huyghe et al., *Hum. Gene Ther.*, 6:1403–1416, 1995.
Jones et al., *Cell*, 17:683–689, 1979.
Kamb et al., *Nature Genetics*, 8:22–26, 1994a.
Kamb et al., *Science*, 2674:436–440, 1994b.
Kaneda et al., *Science*, 243:375–378, 1989.
Kaplan and Smith, *Human Gene Therapy*, 8:1095–1104, 1997.
Kass-Eisler et al, *Proc. Natl. Acad Sci. USA*, 90:1498–11502, 1993.
Kato et al., *J. Biol. Chem.*, 266:3361–3364, 1991.
Klein et al., *Nature*, 327:70–73, 1987.
Kolls et al., *J. of Infectious Diseases*, 171 (3): 570–575, 1996.
Korner and Burgert, *J. of Virol.*, 68 (3):1442–1448, 1994.
Krougliak and Graham, *Human Gene Therapy*, 6:1575–86, 1995.
Le Gal La Salle et al., *Science*, 259:988–990, 1993.
Levine, *Bioessays*, 12:60–66, 1990.
Levrero et al., *Gene*, 101:195–202, 1991.
Lieber et al., *J. of Virol.*, 70:8944–60, 1996.
Lin and Guidotti, *J. Biol. Chem.*, 264:14408–14414, 1989.
Lotze et al, *Curr. Opin. Oncol.*, 4:1116–1123, 1992.
Matsura et al., *Brit. J. Cancer*, 66:1122–1130, 1992.
McBurney et al., *Nucleic Acids Res.*, 19:5755–5761, 1992.
Mercer, *Critic. Rev. Eukar. Gene Express*, 2:251–263, 1992.
Mizrahi, *Process Biochem., (August)*:9–12, 1983.
Montenarh, *Crit. Rev. Oncogen*, 3:233–256, 1992.
Mori et al., *Cancer Res.*, 54:3396–3397, 1994.
Morral et al., *Human Gene Therapy*, 8:1275–1286, 1997.
Mullbacher et al., *Immunol. Cell Biol.*, 67:31–39, 1989.
Myers, EPO 0273085
Neumann et al., *Biotechniques*, 5:444–447, 1987.
Nevins, J., *Cell* 26:213–220, 1981.
Nicolau and Sene, *Biochim. Biophys. Acta*, 721:185–190, 1982.
Nicolau et al., *Methods Enzymol.*, 149:157–176, 1987.
Nobri et al., *Nature* (London), 368:753–756, 1995.
Obrink, *BioEssays.*, 13:227–233, 1991.
Odin and Obrink, *Exp. Cell Res.*, 171:1–15, 1987.
Okamoto et al., *Proc. Natl. Acad. Sci. USA*, 91:11045–11049, 1994.
Orlow et al., *Cancer Res.*, 54:2848–2851, 1994.
Pardoll, D., *Curr. Opin. Oncol.*, 4:1124–1129, 1992.
Perales et al., *Proc. Natl. Acad Sci. USA*, 81:7161–7165, 1994.
Phillips et al., In: *Large Scale Mammalian Cell Culture*, Feder, J. and Tolbert, W. R., eds., Academic Press, Orlando, Fla., USA, 1985.
Potter et al., *Proc. Nat. Acad. Sci. USA*, 81:7161–7165, 1984.
Ragot et al., *Nature*, 361:647–650, 1993.
Renan, *Radiother. Oncol.*, 19:197–218, 1990.
Rich et al., *Hum. Gene Ther.*, 4:461–476, 1993.
Ridgeway, In: *Vectors: A survey of molecular cloning vectors and their uses*, Rodriguez R L, Denhardt D T, ed., Stoneham: Butterworth, pp. 467–492, 1988.
Rippe et al., *Mol. Cell Biol.*, 10:689–695, 1990.
Rosenfeld et al., *Cell*, 68:143–155, 1992.
Rosenfeld et al., *Science*, 252:431–434, 1991.
Sadowski et al., *Gene*, 11: 137–141, 1992.
Sadowski et al., *Nature*, 335:563–564, 1988.
Sambrook, et al., *Molecular cloning: a laboratory manual*. 2nd. New York: Cold Spring Harbor Laboratory Press, 1989.
Serrano et al., *Nature*, 366:704–707, 1993.
Serrano et al., *Science*, 267:249–252, 1995.
Shenk et al., *Cold Spring Harb. Symp. Quant. Biol.*, 44:367–375, 1980.
Song et al., *Human Gene Therapy*, 8:1207–1217, 1997.
Sparer et al., *J. of Virol.*, 71:2277–84, 1997.
Stratford-Perricaudet et al., *Hum. Gene Ther.*, 1:241–256, 1990.
Stratford-Perricaudet et al., *J. of Clin. Invest.*, 90 (2):626–630, 1992.
Sugimara et al, *Environ. Health Perspect.*, 98:5–12, 1992.
Takahashi et al., *Cancer Res.*, 52:2340–2342, 1992.
Top et al., *J. Infect. Dis.*, 124:155–160, 1971.
Tur-Kaspa et al., *Mol. Cell Biol.*, 6:716–718, 1986.
Umbas et al., *Cancer Res.*, 52:5104–5109, 1992.
Urbanelli et al., *Virology*, 173:607–614, 1989.
Vilquin et al., *Human Gene Therapy*, 6 (11): 1391–1401, 1995.
Wagner et al., *Proc. Natl. Acad. Sci.* 87 (9):3410–3414, 1990.
Wagner et al., *Science*, 260:1510–1513, 1993.
Wang et al, *Gene Therapy*, 2:775–783, 1995.
Watt et al., *Proc. Natl. Acad. Sci.*, 83 (2):3166–3170, 1986.
Weinberg and Ketner, *Proc. Natl. Acad. Sci.*, 80:5383–5386, 1983.
Weinberg, *Science*, 254:1138–1146, 1991.
Wong et al., *Gene*, 10:87–94, 1980.
Wu and Wu, *Adv. Drug Delivery Rev.*, 12:159–167, 1993.
Wu and Wu, *Biochemistry*, 27:887–892, 1988.
Wu and Wu, *J. Biol. Chem.*, 262:4429–4432, 1987.
Yang et al., *J. Virol.*, 69:2004–2015, 1995.
Yang et al, *Nature Genetics*, 7: 62–369, 1994.
Yang et al., *Proc. Natl. Acad. Sci. USA*, 87:9568–9572, 1990.
Zhang et al., *Cancer Gene Ther.*, 1:5–13, 1994.

What is claimed is:

1. A method of inducing apoptosis in a cell comprising administering to the cell an adenoviral vector comprising at least one essential viral gene or gene element under the control of a heterologous inducible promoter, wherein the vector lacks a functional copy of one or more of an E1B, E2A, E2B, or E4 gene or gene element, and wherein apoptosis is induced in the cell.

2. The method of claim 1, wherein the viral vector is comprised in a pharmaceutical composition.

3. The method of claim 1, wherein the essential viral gene or gene element under the control of the inducible promoter is selected from the group consisting of E1A, E1B, E2A, E2B, or E4.

4. The method of claim 1, wherein at least two genes or gene elements are non-functional.

5. The method of claim 4, wherein the at least two genes or gene elements are E1A and E1B.

6. The method of claim 4, wherein the adenoviral vector comprises an E3 gene, and wherein the E3 gene is non-functional.

7. The method of claim 3, wherein said essential viral gene or gene element is E4.

8. The method of claim 3, wherein the essential viral gene or gene element is E2A.

9. The method of claim 1, wherein said inducible promoter is a yeast GAL4/TATA promoter.

10. The method of claim 1, wherein said inducible promoter is selected from the group consisting of the auxin inducible promoter, tet-responsive element and an ecdysone hybrid response element.

11. The method of claim 1, wherein said inducible promoter is hormone-responsive, cell-specific, tissue-specific, or disease specific.

12. The method of claim 11, wherein said promoter is hormone-responsive.

13. The method of claim 12, wherein said hormone-responsive promoter is selected from the group consisting of thyroid stimulating hormone ÿ gene, ecdysone hybrid response element, auxin inducible promoter, and mouse mammary tumor virus promoters.

14. The method of claim 11, wherein said promoter is cell-specific.

15. The method of claim 14, wherein said cell-specific promoter is selected from a group consisting of tyrosine, ÿ-fetoprotein, albumin, CC10, and prostate-specific antigen promoters.

16. The method of claim 11, wherein said promoter is tissue-specific.

17. The method of claim 16, wherein said tissue-specific promoter is selected from a group consisting of tyrosine, ÿ-fetoprotein, albumin, CC10, and prostate-specific antigen promoters.

18. The method of claim 11, wherein said promoter is disease-specific.

19. The method of claim 18, wherein said disease-specific promoter is selected from a group consisting of murine MX gene, tyrosinase, ÿ-fetoprotein, albumin, CC10, tet-responsive element and prostate-specific antigen promoters.

20. The method of claim 1, wherein the vector further comprising a heterologous gene.

21. The method of claim 20, wherein said heterologous gene is under the control of a promoter active in eukaryotic cells.

22. The method of claim 21, wherein said promoter is CMV.

23. The method of claim 22, further comprising a polyadenylation signal in operable relation to said heterologous gene.

24. The method of claim 23, wherein said polyadenylation signal is selected from the group consisting of adenovirus, SV40 and bovine growth hormone.

25. The method of claim 21, wherein the heterologous gene is an inducer of apoptosis.

26. The method of claim 25, wherein the inducer of apoptosis is selected from the group consisting of Bax, Bak, Bcl-Xs, Bik, Bid, Harakiri, Ad E1B, Bad, and ICE-CED3 protease.

27. The method of claim 1, wherein the cell is a mammalian cell.

28. The method of claim 27, wherein the cell is a tumor cell.

* * * * *

UNITED STATES PATENT AND TRADEMARK OFFICE
CERTIFICATE OF CORRECTION

| | | |
|---|---|---|
| PATENT NO. | : 7,244,617 B2 | Page 1 of 1 |
| APPLICATION NO. | : 10/677727 | |
| DATED | : July 17, 2007 | |
| INVENTOR(S) | : Bingliang Fang et al. | |

It is certified that error appears in the above-identified patent and that said Letters Patent is hereby corrected as shown below:

In claim 20, column 51, line 14, delete "comprising" and insert --comprises-- therefor.

Signed and Sealed this

Twenty-seventh Day of November, 2007

JON W. DUDAS
*Director of the United States Patent and Trademark Office*

SEQUENCE LISTING

<160> NUMBER OF SEQ ID NOS: 4

<210> SEQ ID NO 1
<211> LENGTH: 15
<212> TYPE: DNA
<213> ORGANISM: Artificial Sequence -continued

```
<220> FEATURE:
<223> OTHER INFORMATION: Description of Artificial Sequence:  Synthetic
      Primer

<400> SEQUENCE: 1
cctaggcaaa atagc                                                    15

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 2
catcatcaat aatatac                                                  17

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 3
tgcctaggca aaatag                                                   16

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 4
catcatcaat aatatac                                                  17
```